United States Patent
Marnfeldt et al.

(10) Patent No.: US 10,363,423 B2
(45) Date of Patent: Jul. 30, 2019

(54) PULSE-BY-PULSE COMPLIANCE VOLTAGE GENERATION FOR AN IMPLANTABLE STIMULATOR

(71) Applicant: Boston Scientific Neuromodulation Corporation, Valencia, CA (US)

(72) Inventors: Goran N. Marnfeldt, Valencia, CA (US); Jess Shi, Porter Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 123 days.

(21) Appl. No.: 15/671,942

(22) Filed: Aug. 8, 2017

(65) Prior Publication Data

US 2017/0333719 A1  Nov. 23, 2017

Related U.S. Application Data

(60) Continuation of application No. 15/065,055, filed on Mar. 9, 2016, now Pat. No. 9,757,565, which is a
(Continued)

(51) Int. Cl.
*A61N 1/36* (2006.01)
*A61N 1/378* (2006.01)
(Continued)

(52) U.S. Cl.
CPC ......... *A61N 1/36146* (2013.01); *A61N 1/025* (2013.01); *A61N 1/08* (2013.01);
(Continued)

(58) Field of Classification Search
CPC ...... A61N 1/36146; A61N 1/025; A61N 1/08; A61N 1/36153; A61N 1/37; A61N 1/378; A61N 1/3605; H03L 1/00
(Continued)

(56) References Cited

U.S. PATENT DOCUMENTS 3,733,498 A  5/1973 Watson
6,181,969 B1  1/2001 Gord
(Continued)

FOREIGN PATENT DOCUMENTS

WO  00/021607  4/2000
WO  2007/070727  6/2007
(Continued)

OTHER PUBLICATIONS

Document # IPCOM000016848D, published at www.ip.com (Jul. 18, 2003).
(Continued)

*Primary Examiner* — Carl H Layno
*Assistant Examiner* — Erin M Piateski
(74) *Attorney, Agent, or Firm* — Lewis & Reese, PLLC

(57) ABSTRACT

Circuitry for generating a compliance voltage (V+) for the current sources and/or sinks in an implantable stimulator device in disclosed. The circuitry assesses whether V+ is optimal for a given pulse, and if not, adjusts V+ for the next pulse. The circuitry uses amplifiers to measure the voltage drop across active PDACs (current sources) and NDAC (current sinks) at an appropriate time during the pulse. The measured voltages are assessed to determine whether they are high or low relative to optimal values. If low, a V+ regulator is controlled to increase V+ for the next pulse; if not, the V+ regulator is controlled to decrease V+ for the next pulse. Through this approach, gradual changes that may be occurring in the implant environment can be accounted for, with V+ adjusted on a pulse-by-pulse basis to keep the voltage drops at or near optimal levels for efficient DAC operation.

20 Claims, 25 Drawing Sheets

Related U.S. Application Data division of application No. 13/861,079, filed on Apr. 11, 2013, now Pat. No. 9,314,632.

(60) Provisional application No. 61/648,403, filed on May 17, 2012.

(51) Int. Cl.

| | | |
|---|---|---|
| *A61N 1/02* | (2006.01) | |
| *A61N 1/08* | (2006.01) | |
| *A61N 1/37* | (2006.01) | |
| *H03L 1/00* | (2006.01) | |

(52) U.S. Cl.
CPC .......... *A61N 1/36153* (2013.01); *A61N 1/37* (2013.01); *A61N 1/378* (2013.01); *H03L 1/00* (2013.01); *A61N 1/3605* (2013.01)

(58) Field of Classification Search
USPC ........................................................ 607/62
See application file for complete search history.

(56) References Cited

U.S. PATENT DOCUMENTS

| | | | |
|---|---|---|---|
| 6,363,277 | B1 | 3/2002 | Dooley et al. |
| 7,177,698 | B2 | 2/2007 | Klosterman et al. |
| 7,400,283 | B1 | 7/2008 | Zhu |
| 7,444,181 | B2 | 10/2008 | Shi et al. |
| 7,483,748 | B2 | 1/2009 | Torgerson et al. |
| 7,539,538 | B2 | 5/2009 | Parramon et al. |
| 7,890,182 | B2 | 2/2011 | Parramon et al. |
| 8,131,377 | B2 | 3/2012 | Shi et al. |
| 2005/0212501 | A1 | 9/2005 | Acatrinei |
| 2006/0066379 | A1* | 3/2006 | Hopsecger ....... H03K 17/04206 327/306 |
| 2007/0038250 | A1 | 2/2007 | He et al. |
| 2007/0097719 | A1 | 5/2007 | Parramon et al. |
| 2007/0100399 | A1 | 5/2007 | Parramon et al. |
| 2007/0135868 | A1* | 6/2007 | Shi ............... A61N 1/36071 607/62 |
| 2007/0276450 | A1 | 11/2007 | Meadows et al. |
| 2008/0015657 | A1 | 1/2008 | Haefner |
| 2008/0048729 | A1* | 2/2008 | Ehrenreich ......... G03F 7/70516 327/63 |
| 2008/0319497 | A1 | 12/2008 | Griffith et al. |
| 2008/0319514 | A1 | 12/2008 | Shi et al. |
| 2009/0018618 | A1* | 1/2009 | Parramon ........ A61N 1/37205 607/60 |
| 2010/0164579 | A1 | 7/2010 | Acatrinei |
| 2010/0211132 | A1 | 8/2010 | Nimmagadda et al. |
| 2011/0110127 | A1 | 5/2011 | Lee |
| 2012/0095529 | A1 | 4/2012 | Parramon et al. |
| 2013/0289665 | A1 | 10/2013 | Marnfeldt et al. |
| 2013/0338732 | A1* | 12/2013 | Foutz ................ A61N 1/378 607/59 |

FOREIGN PATENT DOCUMENTS

| | | |
|---|---|---|
| WO | 2010/096131 | 8/2010 |
| WO | 2011/033489 | 3/2011 |

OTHER PUBLICATIONS

Document # IPCOM000007552D, published at www.ip.com (Apr. 4, 2002).
Emilia Noorsal et al : "A Neural Stimulator Frontend With High-Voltage Compliance and Programmable Pulse Shape for EpiretinalImplants", IEEE Journal of Solid-State Circuits, IEEE Service Center, Piscataway, NJ, USA, vol. 47, No. I, Jan. 1, 2012.
Invitation to Pay Additional Fees regarding PCT Application No. PCT/US2013/036369 dated Jul. 5, 2013.

\* cited by examiner

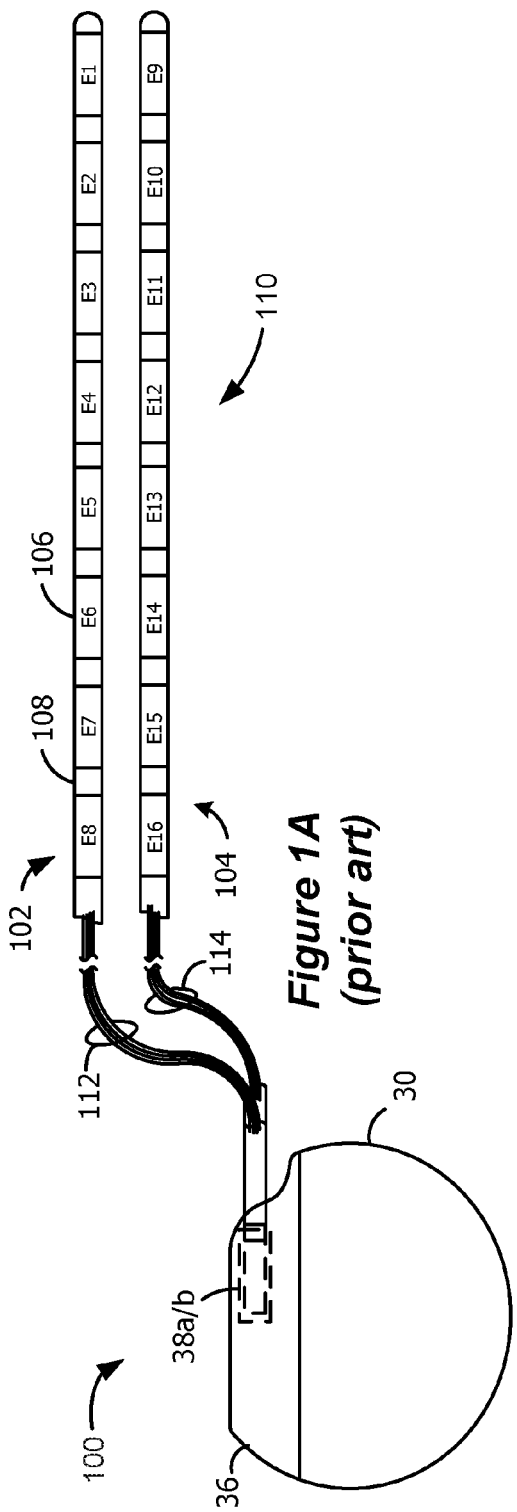
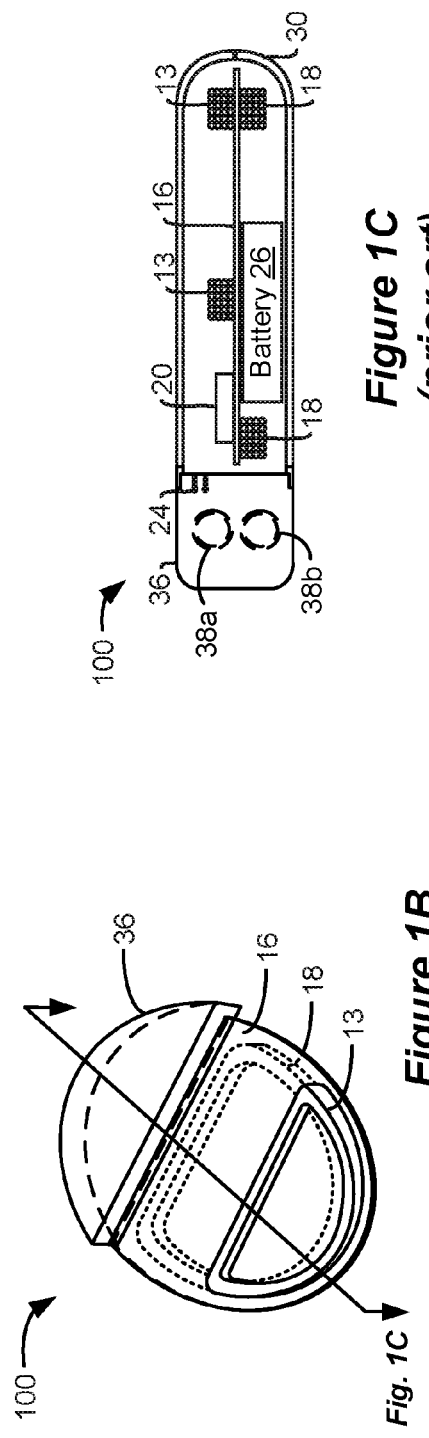
Figure 1A (prior art)
Figure 1B (prior art)
Figure 1C (prior art)

V+ algorithm 90 ly, antennas) are generally present in the IPG 100: a telemetry coil 13 used to transmit/receive data to/from an external controller, and a charging coil 18 for charging or recharging the IPG's battery 26 using an external charger. In this example, the telemetry coil 13 and charging coil 18 are within the case 30, as disclosed in U.S. Patent Publication 2011/0112610. (FIG. 1B shows the IPG 100 with the case 30 removed to ease the viewing of the two coils 13 and 18). However, the telemetry coil 13 may also be mounted within the header 36 of the IPG 100 (not shown).

PULSE-BY-PULSE COMPLIANCE VOLTAGE GENERATION FOR AN IMPLANTABLE STIMULATOR

CROSS-REFERENCE TO RELATED APPLICATIONS

This is a continuation application of U.S. patent application Ser. No. 15/065,055, filed Mar. 9, 2016 (now U.S. Pat. No. 9,757,565), which is a divisional application of U.S. patent application Ser. No. 13/861,079, filed Apr. 11, 2013 (now U.S. Pat. No. 9,314,632), which is a non-provisional filing of U.S. Provisional Application Ser. No. 61/648,403, filed May 17, 2012. Priority is claimed to these applications, and they are incorporated herein by reference.

FIELD OF THE INVENTION

The present invention relates to implantable stimulators, and in particular to circuitry for generating a compliance voltage for the current sources and/or sinks that produce stimulation currents.

BACKGROUND

Implantable stimulation devices generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227. However, the present invention may find applicability in any implantable stimulator.

As shown in FIGS. 1A-1C, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102, 104 couple to the IPG 100 using lead connectors 38a and 38b, which are fixed in a non-conductive header material 36, which can comprise an epoxy for example.

As shown in the cross-section of FIG. 1C, the IPG 100 typically includes an electronic substrate assembly including a printed circuit board (PCB) 16, along with various electronic components 20 mounted to the PCB 16, some of which are discussed subsequently. Two coils (more generally, antennas) are generally present in the IPG 100: a telemetry coil 13 used to transmit/receive data to/from an external controller, and a charging coil 18 for charging or FIGS. 2A and 2B show different current distribution architectures for forming pulses at the electrodes in an IPG 100. FIG. 2A shows an architecture in which each electrode is provided with a dedicated current source (PDAC 50) and current sink (NDAC 60), such as is disclosed in U.S. Pat. No. 6,181,969 for example. The PDAC 50 and NDAC 60 are so named because the amplitude of the analog current they source or sink is digitally controllable (hence, they are Digital-to-Analog Converters, or DACs), and because they are typically made from P-channel and N-channel transistors respectively. As described in U.S. Pat. No. 7,444,181, which is incorporated by reference in its entirety, the PDACs and NDACs can comprise current mirrors, each of which contains at least one output transistor(s) coupled in parallel to set the desired current.

The architecture of FIG. 2A can be used to pass current between any of the N electrodes. For example, and as illustrated, PDAC 50-1 has been programmed to source a constant stimulation current of Iout, while NDAC 60-2 has been enabled to sink a constant current also equal to Iout. The other PDACs and NDACs are disabled in this example. This results in Iout passing out of electrode E1, through the patient's tissue (not shown), and returning back through electrode E2. More than one PDAC 50 or NDAC 60 can enabled at one time to provide more complicated currents in the patient's tissue. As one skilled in the art understands, stimulation currents are typically issued in the form of pulses, which may be uniphasic or biphasic. Any of the electrodes E1-EN can be chosen to either source or sink current.

FIG. 2B shows a distributed architecture in which sourced or sunk current are passed to or from the electrodes using switch matrices 70P and 70N, such as is disclosed in U.S. Patent Publication 2007/0038250 for example. Switching matrix 70P is controllable to source current from any of the PDACs 50 to any of the electrodes, while switching matrix 70N is controllable to sink current from any of the electrodes via NDACs 60. In the example shown, which also involves sending a stimulation current of Iout from E1 to E2, switching matrix 70P has coupled PDAC 50-2 to E1, while switching matrix 70N has coupled NDAC 60-1 to E2. The switching matrices can also be used to send sourced or sunk current to more than one electrode, and the sourced or sunk current from multiple PDACs 50 or NDACs 60 can be sent to the same electrode. Some distributed architectures may only employ a single PDAC 50 and NDAC 60.

Both of the architectures employ decoupling capacitors C1-CN coupled to each of the electrodes. As is well known, decoupling capacitors C1-CN acts as a safety measure to prevent direct DC current injection into the patient.

Regardless of the architecture used, it is important to set the compliance voltage V+ to appropriate levels. The compliance voltage V+ comprises the power supply voltage used by the DAC circuitry that issues the pulses. V+ is generated by boosting the battery voltage, Vbat, and it is desired that V+ be set to an optimal level for the current that the DACs must provide: if too low, the electrodes will not be able to issue pulses of the desired amplitudes; if too high, battery power is unnecessarily wasted.

One approach to setting V+ is disclosed in U.S. Pat. No. 7,444,181, which is summarized here in FIGS. 3 and 4. In the '181 patent, the voltage drops across the active PDACs (Vp1, Vp2, etc.) and NDACs (Vn1, Vn2, etc.) are measured and used to set V+. This occurs by selecting a tap connected to one of the active DACs using a switching matrix 75. The voltage on the selected tap is sent to an Analog-to-Digital (A/D) converter 80, and the digitized value is sent to and stored in control circuitry 85 (e.g., a microcontroller). Because the control circuitry 85 knows a priori the voltage on the other sides of the DACs (V+ for the PDACs, and ground for the NDACs), the voltage drops Vp and Vn can be determined using the digitized tap values.

Operating within the control circuitry 85 is a V+ algorithm 90, which assesses the voltage drops across the active PDACs and NDACs, and sends a control signal to a V+ regulator 95 to set an appropriate value for V+. Generally speaking, the algorithm seeks to bring the voltage drops across the active PDACs (Vp) and NDACs (Vn) within appropriate ranges. These ranges are based on the architectures used for the PDACs and NDACs, which as noted earlier comprise current mirrors which use output transistor(s) to drive the currents. As explained in the '181 patent, it is desired that the output transistor(s) operate in a saturation mode, such that the channels of the transistors are in "pinch off." Keeping the output transistor(s) in saturation requires that the drain-to-source voltage drop across the output transistor(s), Vds (i.e., Vp and Vn), be greater that the gate-to-source voltage (Vgs) minus their threshold voltage (Vt). Operation in saturation is desired for providing the proper amount of current: if Vds is too low and the output transistor(s) are operating in sub-saturation, the DACs will not be able to provide the desired current. However, it is also desired that Vds not be too high, because unnecessary additional voltage drop across the output transistor(s) merely wastes power, which is highly undesirable in the battery-operated IPG 100. Due to the differences inherent in the P-channel and N-channel transistors used in the PDACs and NDACs, the desired ranges for Vp and Vn disclosed in the '181 patent are different: e.g., 1.5 to 2.1V for Vp, and 1.2 to 1.8V for Vn. Essentially, the V+ algorithm 90 tries to adjust V+ until Vp and Vn for all the active DACs are within these ranges if possible. (It may not be possible for all of the active DACs to be within these ranges given possible differences in the currents used and difference in tissue resistance between the electrodes).

The V+ algorithm 90 of the '181 patent is described further in FIG. 4. Normally, the algorithm 90 would start with the compliance voltage, V+ at its maximum value (e.g., V+(max)=18V), and as it operates it gradually reduces V+ to a desired level. The algorithm starts by first acquiring the voltage drops for the active NDACs (Vn1, Vn2, etc.), which measurements are preferably made toward the end of the pulses. Next, a minimum of these voltages (Min(Vn)) is determined. This minimum voltage would suggest the NDAC most at risk to be in sub-saturation, and hence in this embodiment of the algorithm is considered the most efficient to track. Accordingly, the algorithm 90 next asks how that minimum value compares relative to the range of guard band voltages for the NDACs. Essentially, if Min(Vn) is higher than the maximum guard band voltage for the NDACs (e.g., 1.8V), the compliance voltage V+ is decreased, because it can be inferred that all NDACs are at this point operating with voltage drops that are too high to be optimal from a power consumption standpoint. To expedite the iterative nature of the algorithm, the extent to which the compliance voltage V+ is decreased scales with the extent to which Min(Vn) exceeds the upper guard band voltage for the NDACs. Thus, if Min(Vn) is very high above the guard band, the compliance voltage is decreased by a large amount, but if barely above the guard band the compliance voltage is decreased by a small amount.

As the compliance voltage V+ is adjusted, Min(Vn) will eventually come within the guard band range (e.g., between 1.2V and 1.8V), and the PDACs can then be assessed. The algorithm 90 then measures the voltage drops for the active PDACs (Vp1, Vp2, etc.). Next, a minimum of these voltages (Min(Vp)) is determined, and the algorithm 90 then proceeds as described earlier for the NDACs by adjusting V+ until the Min(Vp) is brought within its guard band range (e.g., between 1.5V and 2.1V). At this point, V+ is now set for the IPG at value V+(opt).

FIG. 5 further illustrates the operation of V+ algorithm 90, and assumes for simplicity that only one PDAC and one NDAC are operating to provide constant current pulses at electrodes E1 and E2, and thus each measured Vn or Vp comprises the minimum for purposes of the algorithm 90. As shown, the compliance voltage V+ starts at a maximum value (V+(max)). Then Vn is measured at the end of the pulse across the active NDAC that is sinking current from electrode E2. If Vn is higher than its guard band range, the V+ algorithm reduces V+, and Vn is then measured on a subsequent pulse. Eventually as V+ falls, Vn is brought within its guard band, and the V+ algorithm 90 can start monitoring Vp at the end of the pulses for the active PDAC that is sourcing current to electrode E1. If Vp is higher than its guard band range, the V+ algorithm reduces V+, and Vp is again measured on a subsequent pulse. Eventually Vp is brought within its guard band, at which point V+ determines that the current value for V+ is optimal, and thus V+ is set by algorithm 90 to that optimal value, V+(opt).

BRIEF DESCRIPTION OF THE DRAWINGS

FIGS. 1A-1C illustrate different views of an implantable medical device, specifically an Implantable Pulse Generator (IPG).

DETAILED DESCRIPTION

As an IPG operates, the inventors recognize that there can be changes that might require resetting V+(opt). For example, the electrodes may shift in the patient as the patient moves. Such movement can change the resistance R of the tissue through which the current pulses flow, and thus change the voltage drop, Vr, across the tissue (see FIG. 6B). Because V+ is a function of Vr, such changes in Vr could suggest that V+(opt) should also be changed.

The inventors disclose improved circuitry for generating a compliance voltage (V+) for the current sources and/or sinks in an implantable stimulator device. The improved V+ generation circuitry assesses whether V+ is optimal for a given pulse, and if not, adjusts V+ for the next pulse. The circuitry uses amplifiers to measure the voltage drop across active PDACs (current sources) and NDACs (current sinks) at an appropriate time during the pulse. The measured voltages are assessed to determine whether they are high or low relative to optimal values. If they are low, a V+ regulator is controlled (e.g., enabled) to increase V+ for the next pulse; if not, the V+ regulator is controlled (e.g., disabled) to decrease V+ for the next pulse. Through this approach, gradual changes that may be occurring in the implant environment can be accounted for, with V+ adjusted on a pulse-by-pulse basis to keep the voltage drops at or near optimal levels for efficient DAC operation.

Figure 2B:
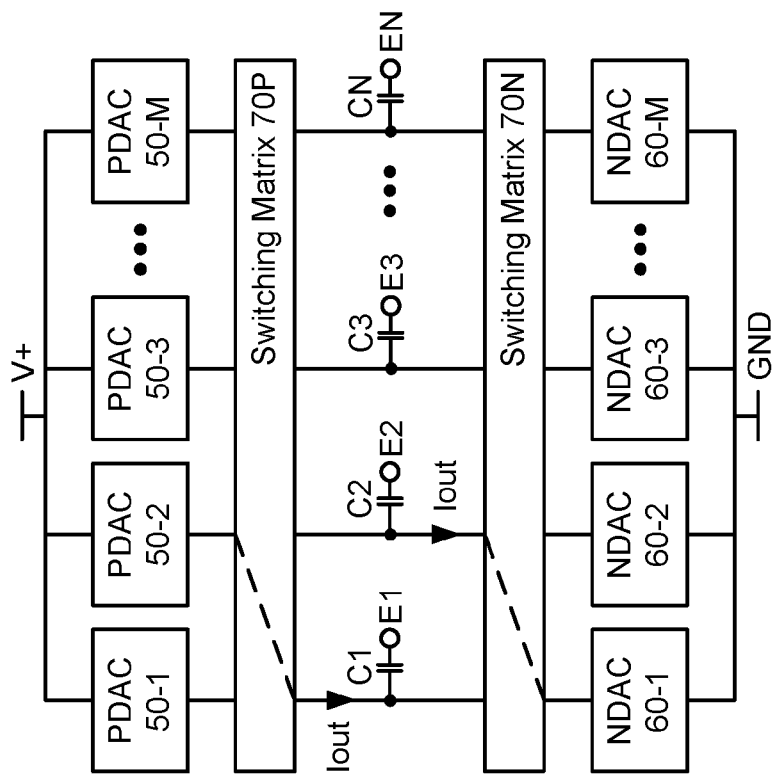
FIGS. 2A-2B illustrate various current distribution architectures for forming pulses at electrodes of the IPG.
Figure 2A:
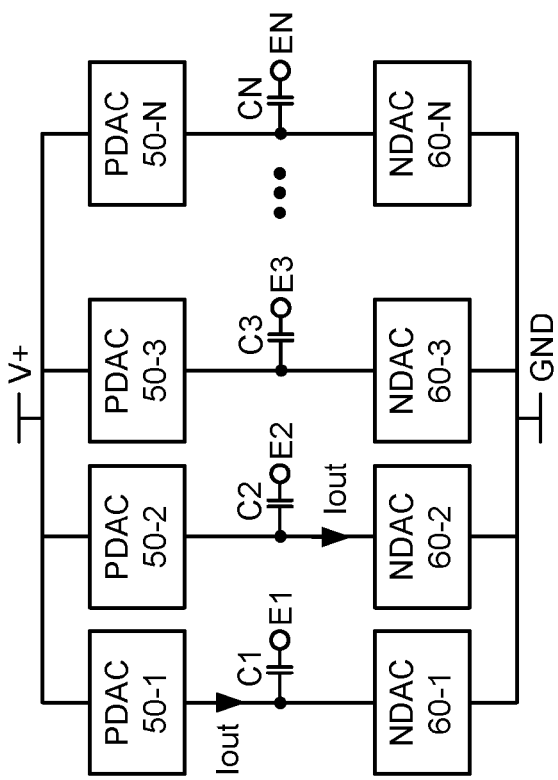
Figure 3:
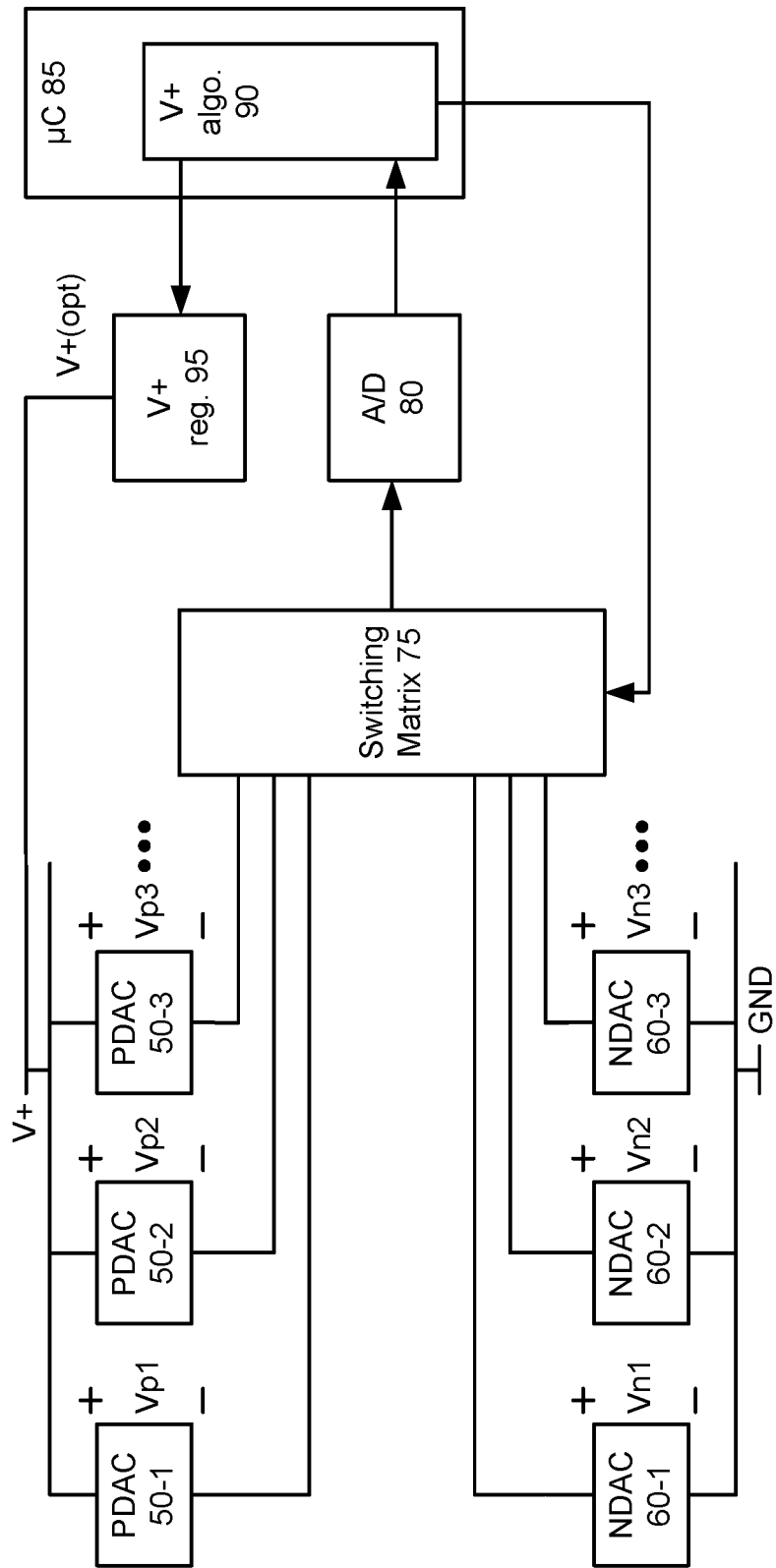
FIG. 3 illustrates a block diagram for circuitry used to set a compliance voltage of the IPG in the prior art.
Figure 4:
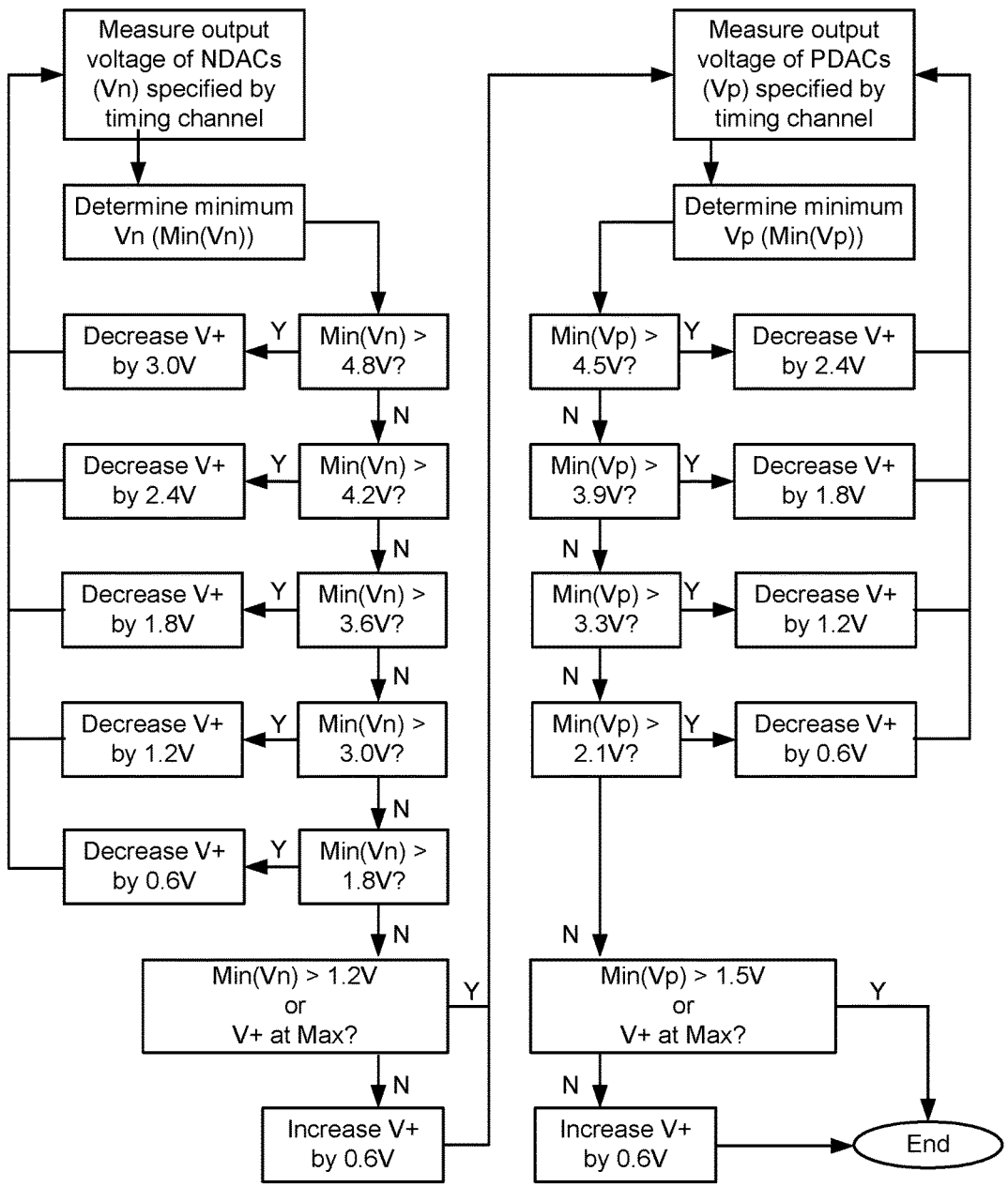
FIG. 4 illustrates a flowchart illustrating a compliance voltage algorithm for setting the compliance voltage of the IPG in the prior art.
Figure 5:
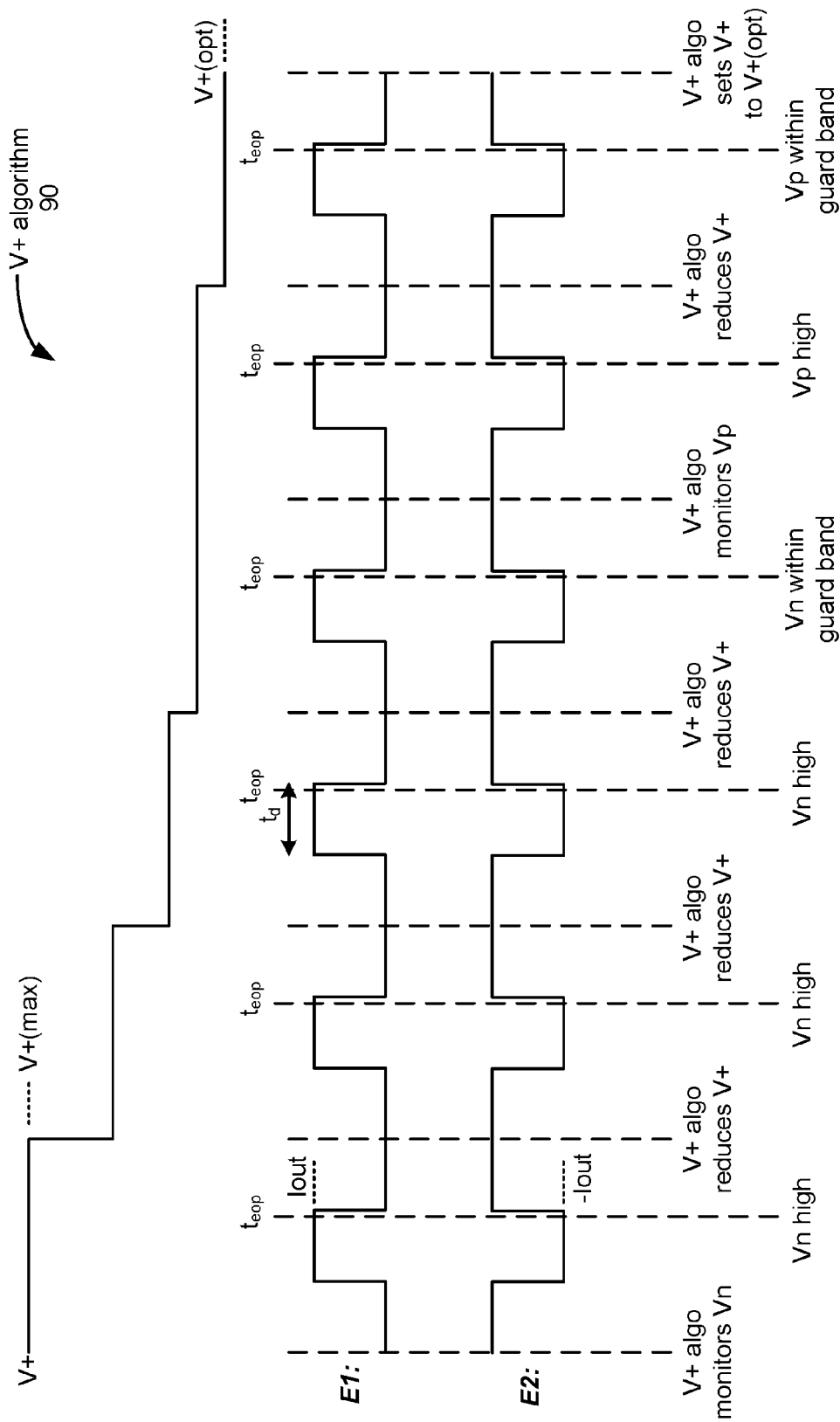
FIG. 5 illustrates waveforms illustrating the setting of the compliance voltage by the compliance voltage algorithm of FIG. 4 in the prior art.
Figure 6A:
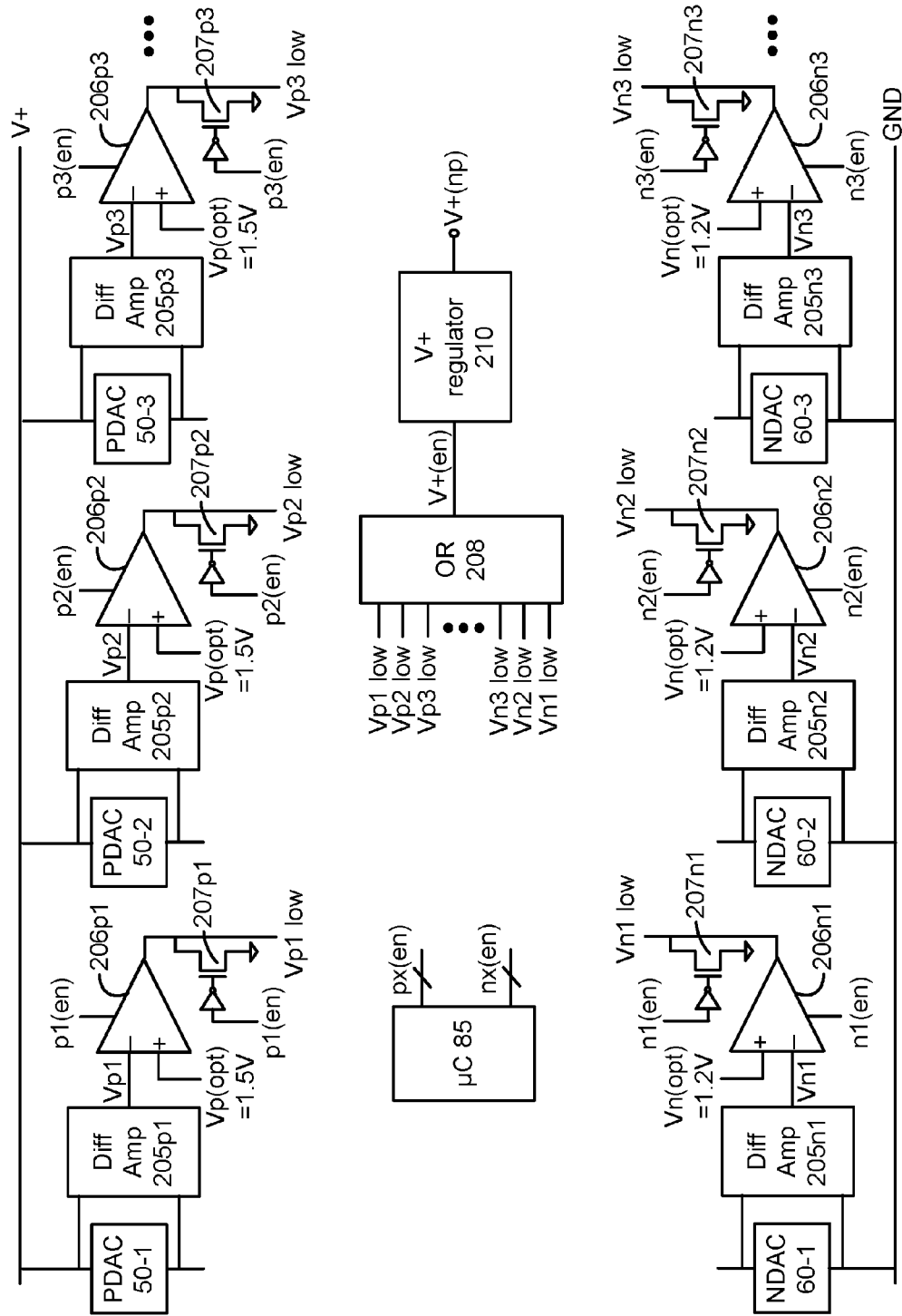
FIG. 6A illustrates an improved compliance voltage generation circuit, in accordance with an embodiment of the present invention, using an OR gate.

A first example of improved V+ generation circuitry 200 is shown in FIG. 6A. Shown are a number of PDACs 50 and NDACs 60, which can couple to the electrodes (not shown) in either a dedicated (FIG. 2A) or distributed (FIG. 2B) architecture. Each DAC is coupled to a measurement stage comprising a differential amplifier (diff amp) 205, a comparator 206, and a pull-down transistor 207. The differential amplifiers 205 discern the analog voltage drop across each DAC (Vp1, Vp2, . . . , Vn1, Vn2, . . . ). These analog values are input to the comparators 206, which compare the voltage drop to optimal values (Vp(opt)=1.5V; Vn(opt)=1.2V), and which issue a digital signal indicative whether the analog voltage is high ('0') or low ('1') relative to the optimal values. Because these digital signals are high ('1') when Vp or Vn are lower than their optimal voltages, these digital signals are denoted as "Vpx low" or "Vnx low" in FIG. 6A. These digital signals are input to an OR gate 208, which controls a V+ regulator 210 to produce the compliance voltage for the next pulse, V+(np). Vp(opt) and Vn(opt) can be produced by tunable bandgap reference voltage generators for example (not shown).

By way of quick overview, if any of the inputs to the OR gate 208 indicate a low voltage for any of the voltage drops, the V+ regulator 210 is enabled by setting V+(en) high ('1'), thereby increasing V+(np); if no inputs indicate a low voltage, the V+ regulator 210 is disabled by setting V+(en) low ('0'), which allows V+(np) to decrease as will be explained subsequently. In this way, V+(np) is adjusted on a pulse-by-pulse basis, with the goal of keeping the voltage drops across the DACs at or slightly above optimal values. As noted earlier, if these voltages drops are too low, the DACs will operate sub-saturation, and will be incapable of producing desired currents.

Figure 6B:
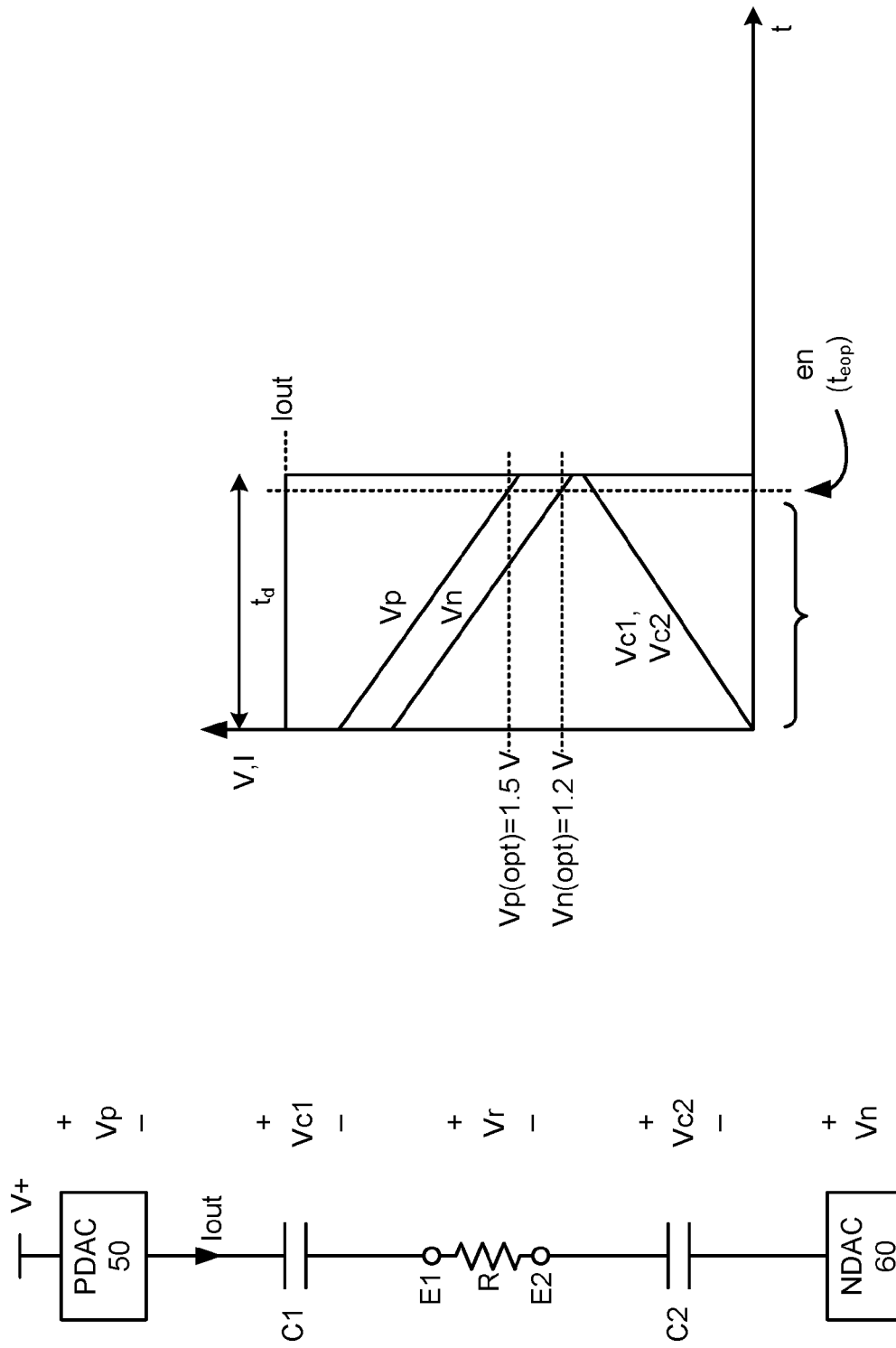
FIG. 6B illustrates various voltages generated during the operation of the improved compliance voltage generation circuit of FIG. 6A.

Each of the measurement stages at each DAC receives an enable signal (en), which informs the comparators 206 when to compare the inputs, i.e., which times the measurement. For normal square current pulses, these enable signals would typically issue near the end of the pulses. FIG. 6B illustrates why this is logical, and shows the passage of a current pulse from electrode E1 to electrode E2 as described earlier, and the circuitry involved, including (in this example) one PDAC 50, the decoupling capacitor connected to E1, the patient's tissue R, the decoupling capacitor connected to E2, and one NDAC 60. Each of these serially-connected circuit elements will drop some portion of the compliance voltage V+, i.e., V+=Vp+Vc1+Vr+Vc2+Vn. The voltage drop through the tissue, Vr, is difficult to know a priori, but in any event will remaining constant over the duration of the pulse. By contrast, the voltage drop across the decoupling capacitors C1 and C2, Vc1 and Vc2, will increase as current is injected through them. Because V+ is constant, Vp and Vn must decrease in accordance with above equation to offset the increase in the voltage across the decoupling capacitors. Therefore, Vp and Vn are at their worst cases (lowest values) at or near the end of the pulse (at time $t_{eop}$). Because the output transistor(s) in the DACs are therefore at greatest risk of entering sub-saturation at $t_{eop}$, this is a proper time to measure the voltage drops, and set V+(np) accordingly.

Returning to FIG. 6A, the various enable signals for each of the measurement stages (p1(en), p2(en), . . . , n1(en), p2(en), . . . ) are ultimately issued by control circuitry 85. As the control circuitry 85 is already responsible for programming the DACs to issue the pulses, it already knows when the end of the pulse will occur, and can issue the enable signals at appropriate times.

As well as timing the measurements, the enable signals can also be used to select the active DACs for measurement. Assume for example that PDAC 50-1, PDAC 50-3, and NDAC 60-2 are currently active to source or sink current, thereby providing a current pulse to the patient's tissue. At the end of the pulse ($t_{eop}$), p1(en), p3(en) and n2(en) are set high ('1') by the control circuitry 85 (which again knows which DACs are active) to enable comparators 206p1, 206p3, and 206n2, which allows Vp1 low, Vp3 low, and Vn2 low to be passed to OR gate 208. The other enable signals (p2(en), n1(en), and n3(en)) for the inactive DACs are set low ('0'). These low enable signal are received at an inverter in the inactive measurement circuits, which turns on pull-down transistors 207, which forces the outputs of these comparators 206 low ('0'). Because these outputs are low, they cannot affect the output of the OR gate 208, and thus in effect comprise don't care values. By contrast, in the measurement circuitry for the active DACs, the high enable signals will be inverted low, and thus not turn on the pull down transistors 207 in those circuits, which allows these comparators 206 to output meaningful signals to the OR gate 208 indicative of the measurement. In short, only meaningful measurements are sent to the OR gate 208 via control of the various enable signals.

Figure 7A:
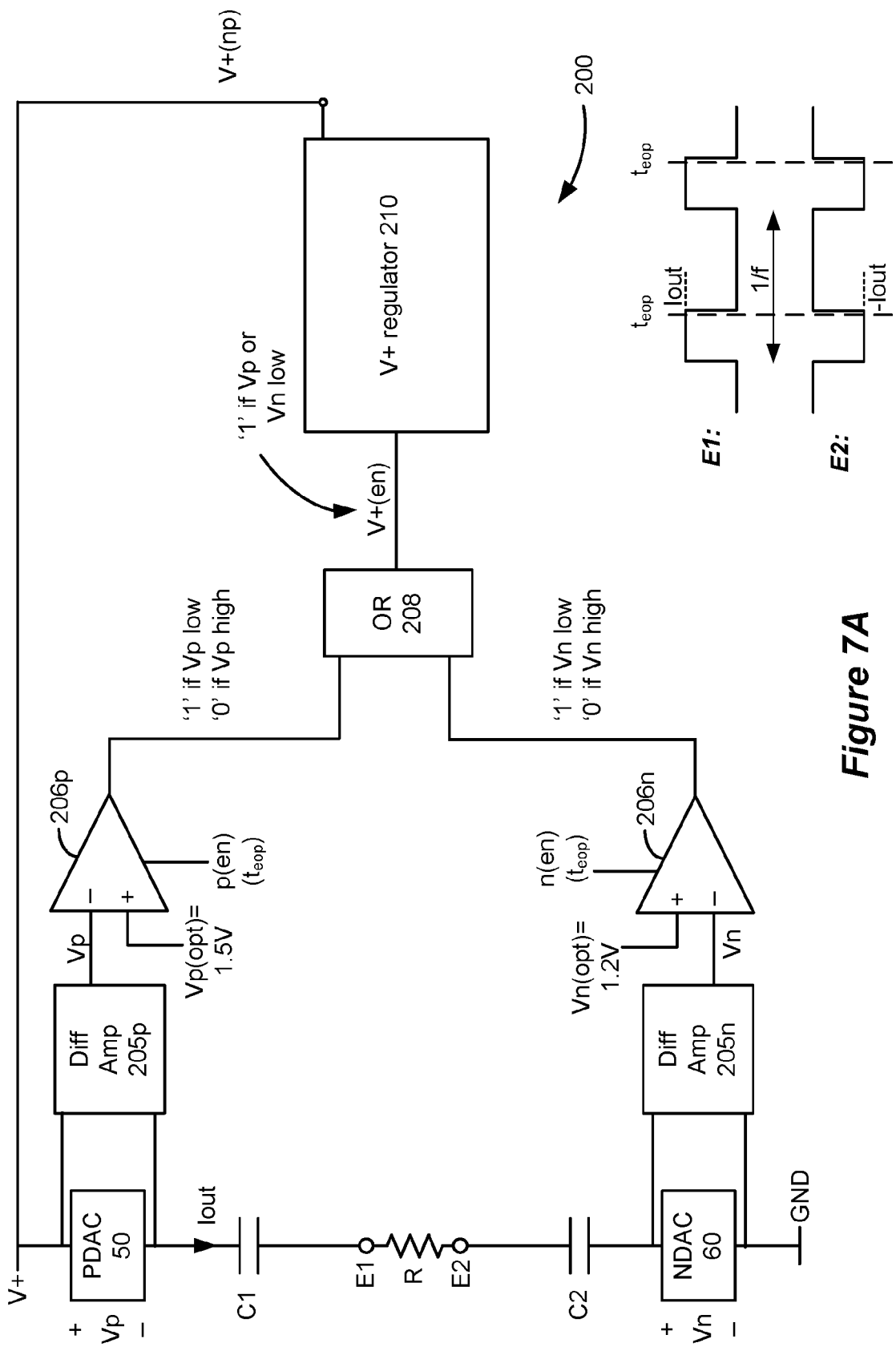
FIGS. 7A-7D illustrate a simple example of the improved compliance voltage generation circuit of FIG. 6A and illustrates its operation.

FIG. 7A shows a simple example of V+ generation circuitry 200, with many of the details of FIG. 6A excluded. Two current generators are used to provide the desired current, Iout, from electrode E1 to electrode E2, with PDAC 50 sourcing the current to E1 and NDAC 60 sinking the current from E2. Diff amps 205 resolve the analog voltage drops across these generators (Vp, Vn), and each are compared to optimal values (Vp(opt), Vn(opt)) at the end of the pulse ($t_{eop}$). If either Vp or Vn is low in comparison to the optimal values, i.e., if either of the outputs of comparators 206 is a '1', the output of the OR gate 208 (V+(en)) will be a '1', which will enable the V+ regulator 210 to increase the compliance voltage V+(np) for the next pulse. This is done in the hopes that neither Vp nor Vn will be low, and therefore will be sufficient to drive the current, for that next pulse.

Figure 7B:
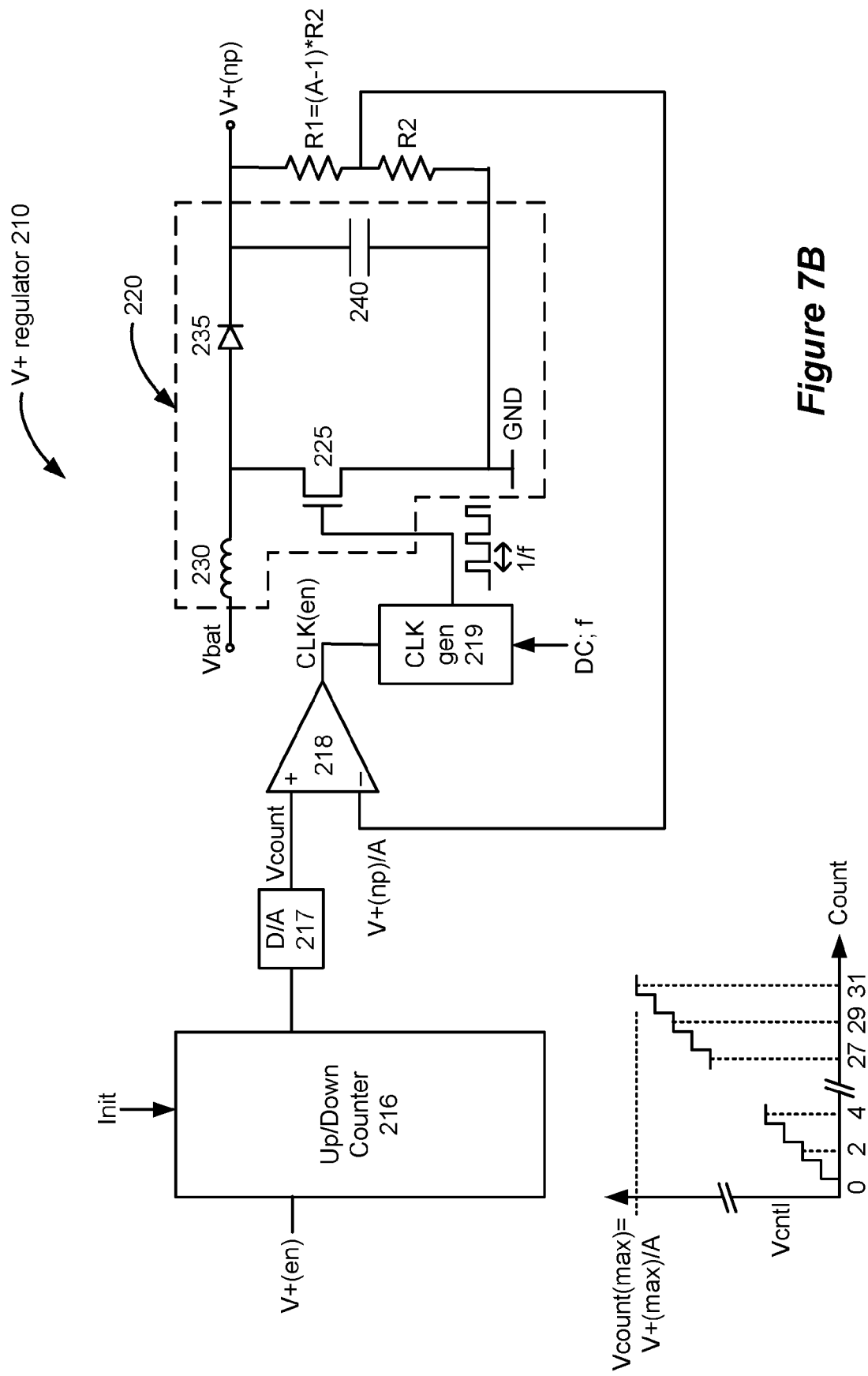

Further details of the V+ regulator 210 are shown in FIG. 7B. As shown, V+(en) is input to an up/down counter 216, which outputs a digital value indicative of the current count. The count of the up/down counter 216 can be initialized by the control circuitry 85 to a proper value at a control input, Init. Thereafter, the current count, in this simple example, is incremented if V+(en)=1, or decremented if V+(en)=0. (Another embodiment for the up/down counter circuitry is discussed later with respect to FIG. 7D). This digital count value is converted to an analog signal, Vcount, by D/A converter 218. As shown in the graph at the bottom of FIG. 7B, the up/down counter 216 can count between 0 and 31, and thus Vcount can comprise 32 different voltages, although this is merely exemplary and different resolutions could be used as well. Vcount is provided to the non-inverting input of a comparator 218, where it is compared to the current output of the V+ regulator 210, V+(np), as scaled by a voltage divider comprising resistors R1 and R2. The values for R1 and R2 will be high to prevent unnecessary power loss (e.g., in the M-ohm range), and are chosen to equate the maximum count voltage (Vcount(max)) with a maximum value for the compliance voltage that the V+ regulator 210 can produce (V+(max)). For example, if these maximum values are related by the scalar 'A' as shown in the equation of FIG. 7B, then R1 and R2 are chosen to produce a voltage V+(np)/A at the inverting input of the comparator 218.

If Vcount exceeds this feedback voltage (V+(np)/A), the comparator 218 outputs a high value (CLK(en)=1) to a clock generator 219, which causes it to produce a clock signal of a particular duty cycle (DC) and frequency (f). The duty cycle and frequency may be programmed into the clock generator 218 by the control circuitry 85, or such parameters may be hard-wired in the circuitry. One skilled in the art will realize that the duty cycle and frequency will affect the rate at which V+(np) will increase, and such values may be empirically determined based on the frequency of the pulses being produced.

The clock signal is sent to a boost converter 220, which is of conventional design, and in particular to the gate of a pulse width modulation (PWM) transistor 225. During portions of the duty cycle when the clock signal is high, PWM transistor 225 turns on, and inductor 230 is shorted to ground and draws current. When the clock signal returns to zero, the transistor 225 is turned off, causing the inductor 230 to inject its stored current through a diode 235 to a storage capacitor 240 where the compliance voltage V+(np) is formed. V+(np) is then fed back to the current distribution circuitry to provide power to drive the next pulse.

Normally, the storage capacitor 240 on a boost converter is relatively large (e.g., 28 µF) to hold and filter the generated voltage. In V+ regulator 210, the storage capacitor 240 is significantly smaller (e.g., 1 µF), which allows V+(np) to change more rapidly in time to power the next pulse. Rapid response in adjusting V+(np) is further assisted by increasing the frequency of the clock signal (e.g., to 1 MHz), and by lowering the inductance of the inductor 230 (e.g., to 10 µH). Such values for the components in V+ regulator 210 allow V+(np) to change suitably quickly relative to the period between the pulses. Routine experimentation and simulation of these values can further improve or control V+(np) response if necessary.

If Vcount does not exceed V+(np)/A, the comparator 218 outputs a low value (CLK(en)=0) to the clock generator 219, which disables the clock signal. With the gate of PWM transistor 225 shut off, the boost converter 220 no longer operates, and V+(np) will begin to fall. The rate of decline of V+(np) will be governed by the storage capacitor 240 in the V+ regulator 210 and other resistances inherent in the circuitry, as one skilled in the art will appreciate.

Figure 7C:
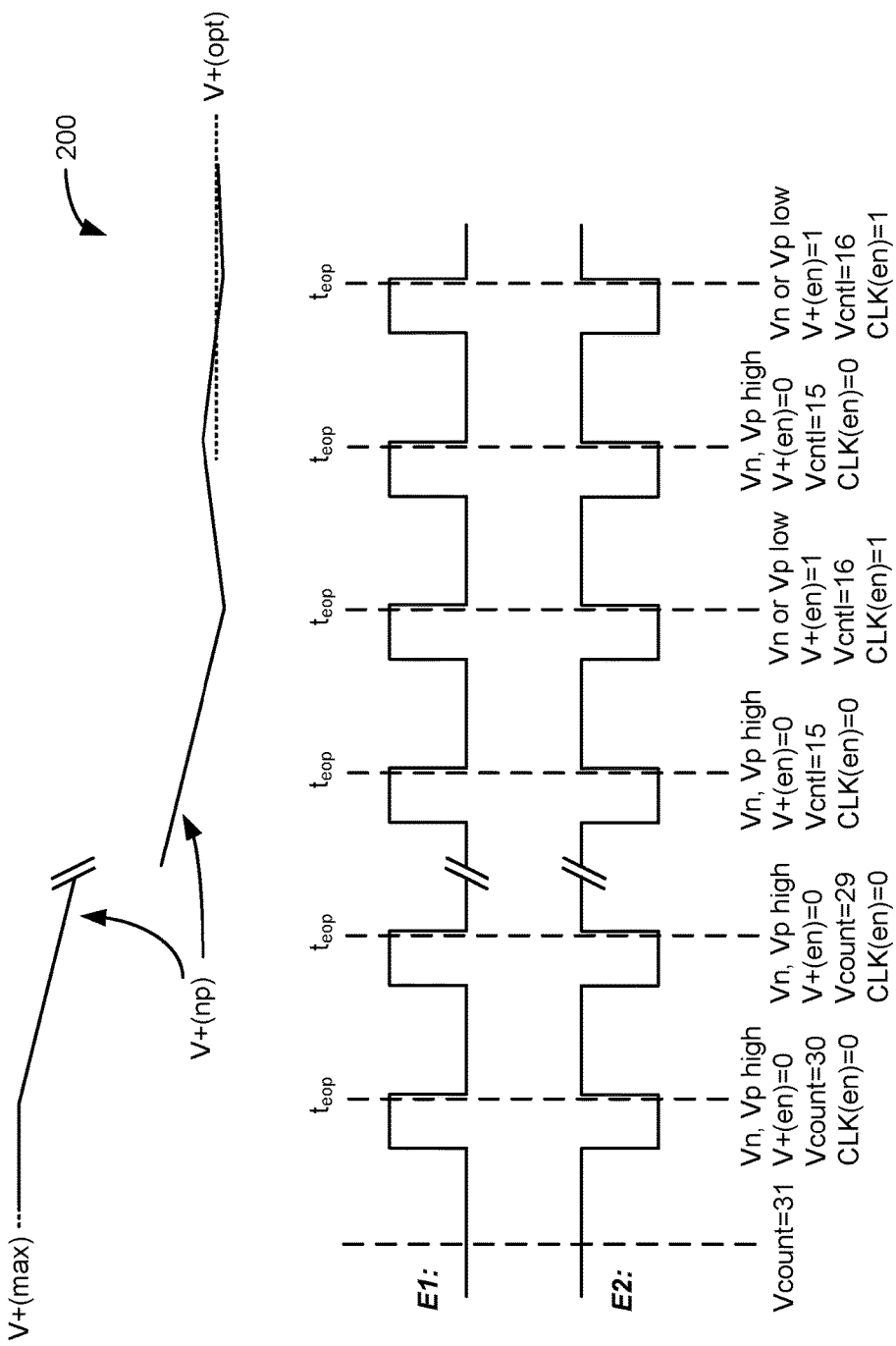

Further details of the operation of V+ generation circuitry 200 and the V+ regulator 210 are illustrated in FIG. 7C. As shown, it is preferred to start optimization with V+(np) initialized to V+(max). While this will likely result in voltage drops across the DACs, Vp and Vn, that are well above their optimal values, Vp(opt) and Vn(opt), and thus initially wasteful of power, it assured that the pulses will have sufficient drive power, and therefore provide adequate therapy to the patient. Vcount is also initialized to its maximum value, which in this example indicates a count of 31.

Vp and Vn are measured at the end of a first pulse, and are judged by comparators 206 to be high, which is not surprising because V+(np) is currently at it maximum. Because all inputs to OR gate 208 are low, V+(en) is set low, and the up/down counter 216 is decremented to 30. This decreased value for Vcount is thus smaller than the fed back, scaled, maximum voltage for V+(np), and comparator 218 outputs a '0' (CLK(en)), which disables the clock generator 219. This turns off the boost converter 220, and V+(np) begins to fall as shown. Vp and Vn are measured at the second pulse, and are still too high, because V+(np) has not fallen quickly enough. The process thus continues similarly: V+(en) is still set low, the count is decremented (to 29), CLK(en)=0, the boost converter 220 is disabled, and V+(np) continues to fall. At some point in the future, V+(np) has fallen significantly, but Vp and Vn are still too high compared to their optimal values. The count continues to decrement (to 15 in the example shown), and the boost converter remains off, and V+(np) continues to fall.

Eventually, V+(np) will fall to such an extent that either Vp or Vn are now too low. At this point, either or both of the measurement circuits for PDAC 50 or NDAC 60 will output a '1' to the OR gate 208, and V+(en) will be set high. The count will be incremented (to 16), which will now cause comparator 218 to set CLK(en)=1. This turns on the clock signal, which enables the boost converter 220, and V+(np) now begins to rise, which will tend to increase Vp and Vn. If on the next pulse, Vp and Vn are once again too high, V+(en)=0, the count is decremented (to 15), the boost converter 220 is again shut off, and V+(np) begins to fall. In short, eventually the circuitry establishes a value for Vcount (between 15 and 16 in this example), and the V+ generation circuitry 200 will stabilize around this value, with the V+ regulator 210 shutting off and turning on as necessary to stay near this value. The result is that Vp and Vn will hover at or just slightly above, their optimal values, Vp(opt) and Vn(opt), which as noted earlier is optimal from an energy efficiency standpoint.

Such pulse-by-pulse adjustment of V+(np) continues to occur even if the environment of the IPG changes. Returning to FIG. 7A again, assume for example that the resistance R of the patient's tissue changes over time, which could occur for any number of reasons. If the resistance increases, Vr will increase, meaning that the currently-established value for V+(np) will no longer be sufficient to drive the desired current, Iout. If the resistance decreases, Vr will decrease, meaning that the currently-established value for V+(np) will be sufficient to drive the current, but needlessly wastes power. Either condition is detected by monitoring Vp and Vn, and is compensated by either raising V+(np) if either Vp or Vn are too low, or decreasing V+(pn) if both are too high.

Figure 7D:
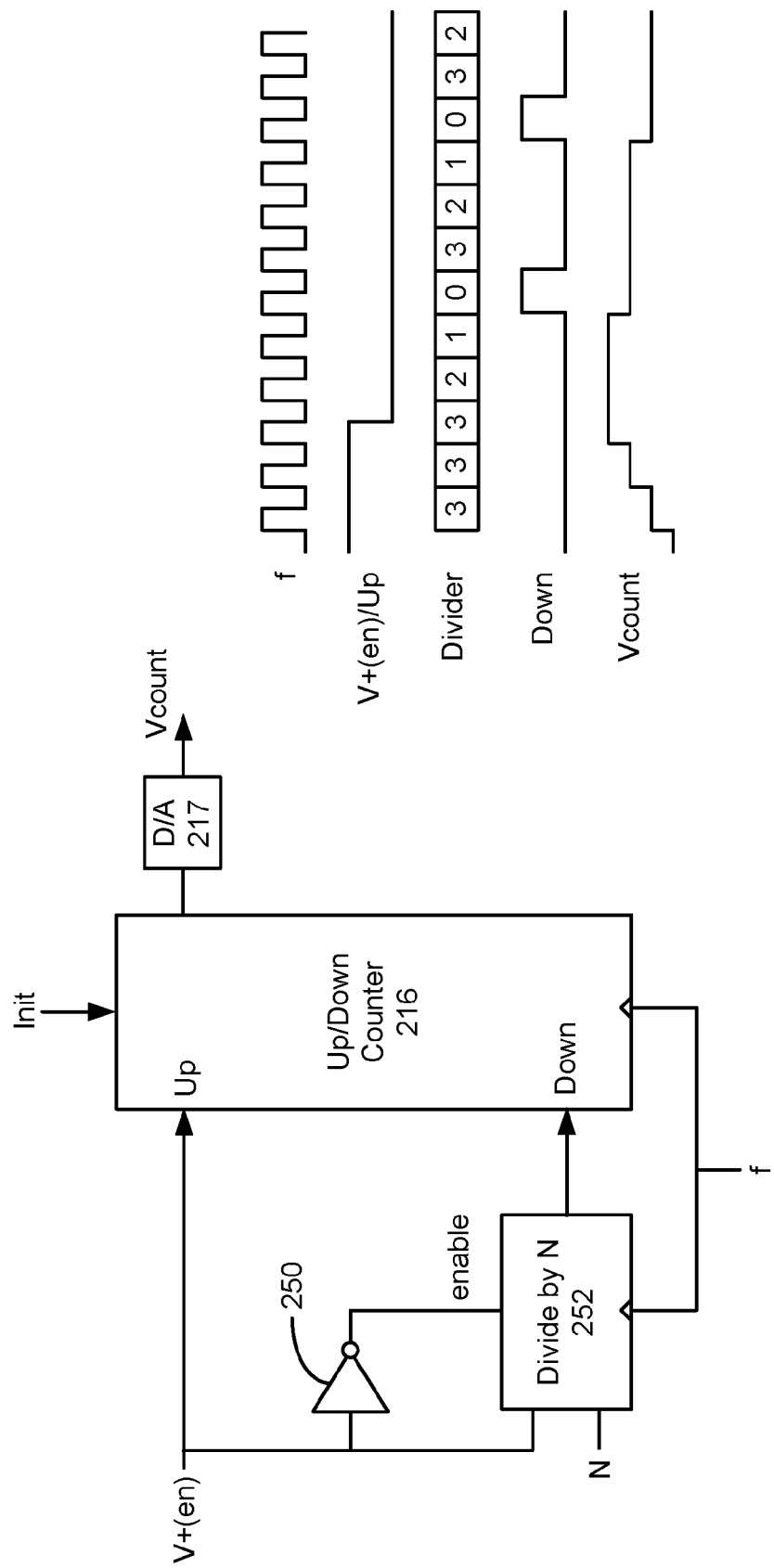

The up/down counter circuitry 216 can be modified as shown in FIG. 7D to address the possibility that the V+ regulator 210 may produce a value for V+(np) that undershoots an optimal value. This can occur if the storage capacitor 240 in the boost converter 220 cannot discharge quickly enough relative to the desire to reduce V+(np), i.e., when V+(en)=0. Assume V+(np) is initialized to V+(max), as just discussed. The feedback in the circuit will call for a reduction in V+(np) by setting V+(en)=0, which reduces the count in the up/down counter circuitry 216. If V+(np) falls too slowly, the count may eventually equal zero, even though V+(np) is still too high. Later when V+(np) has eventually fallen to the point when it is too low to be optimal (i.e., V+(en)=1), the count is incremented (to 1), in the hope that comparator 218 will issue CLK(en)=1 to turn on the clock signal from the clock generator 219. But because V+(np) is still relatively high to a count of one, the comparator instead issues CLK=0, and the clock signal and boost converter 220 are not turned on. As a result, V+(en) will continue to fall and undershoots its optimal value. This is desired because during such periods of undershoot the DACs may not be capable for producing their desired currents.

The solution to this issue is to not count down faster than that storage capacitor 240 (i.e., V+(np)) can discharge, and the rate at which the count is decremented can be modified by a divide by N circuit 252, as shown in FIG. 7D. When V+(en)=0, indicating a desire to reduce V+(np), inverter 250 enables the divide by N circuitry 252, such that the up/down counter 216 is only instructed to decrement once every N times that V+(en)=0. The value for N can be programmed into the divide by N counter by the control circuitry 85, and can be determined by routine modeling or experimentation so that Vcount tracks V+(np) downward. Both the divide by N circuit 252 and the up/down counter 216 are clocked at the same frequency as the current pulses that are being issued. Because the divide by N circuitry receives V+(en), it can ensure that a down count is issued to the up/down counter only when V+(en)=0 for N periods in a row; if V+(en)=1 before N periods have occurred, the divide by N circuit 252 is not enabled and resets. Note that division is not necessary when it is desired to increase the count, i.e., when V+(en)=1. This is desired because if V+(np) is too low, it is desired to turn on the boost converter 220 immediately to raise it to an optimal level. Waveforms illustrating the operation of the circuitry are provided at the right of FIG. 7D, assuming that N=4.

Figure 8:
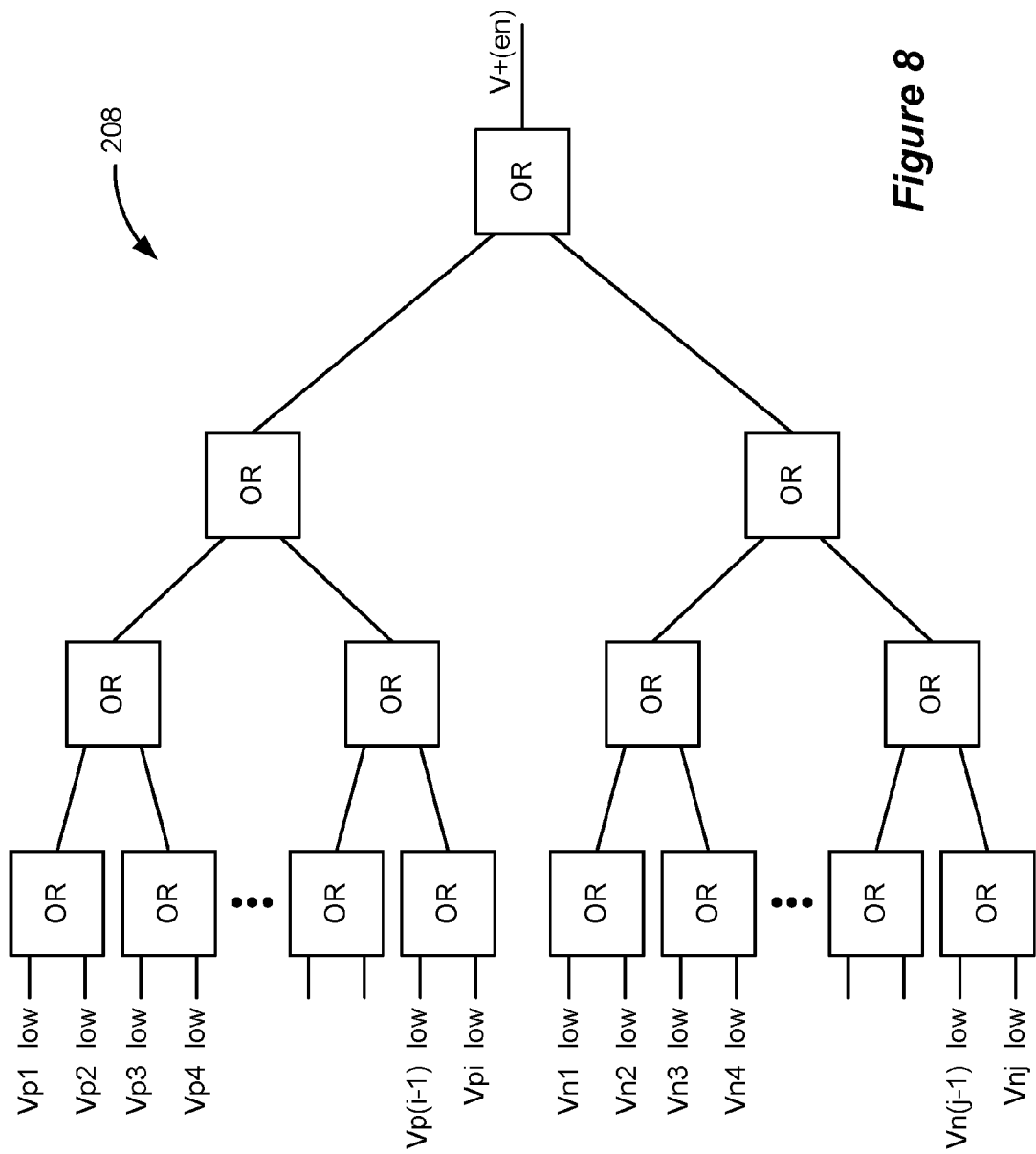
FIG. 8 illustrates an OR gate useable in the improved compliance voltage generation circuit.

FIG. 8 shows how the multi-input OR gate 208 of FIG. 6A can be formed by a cascading array of more-traditional two-input OR gates. One skilled in the art will appreciate without the need for explanation that V+(en) will be high if any of the inputs are high. OR gate 208 can also be constructed in other manners, using other types of logic gates or circuits.

Figure 9A:
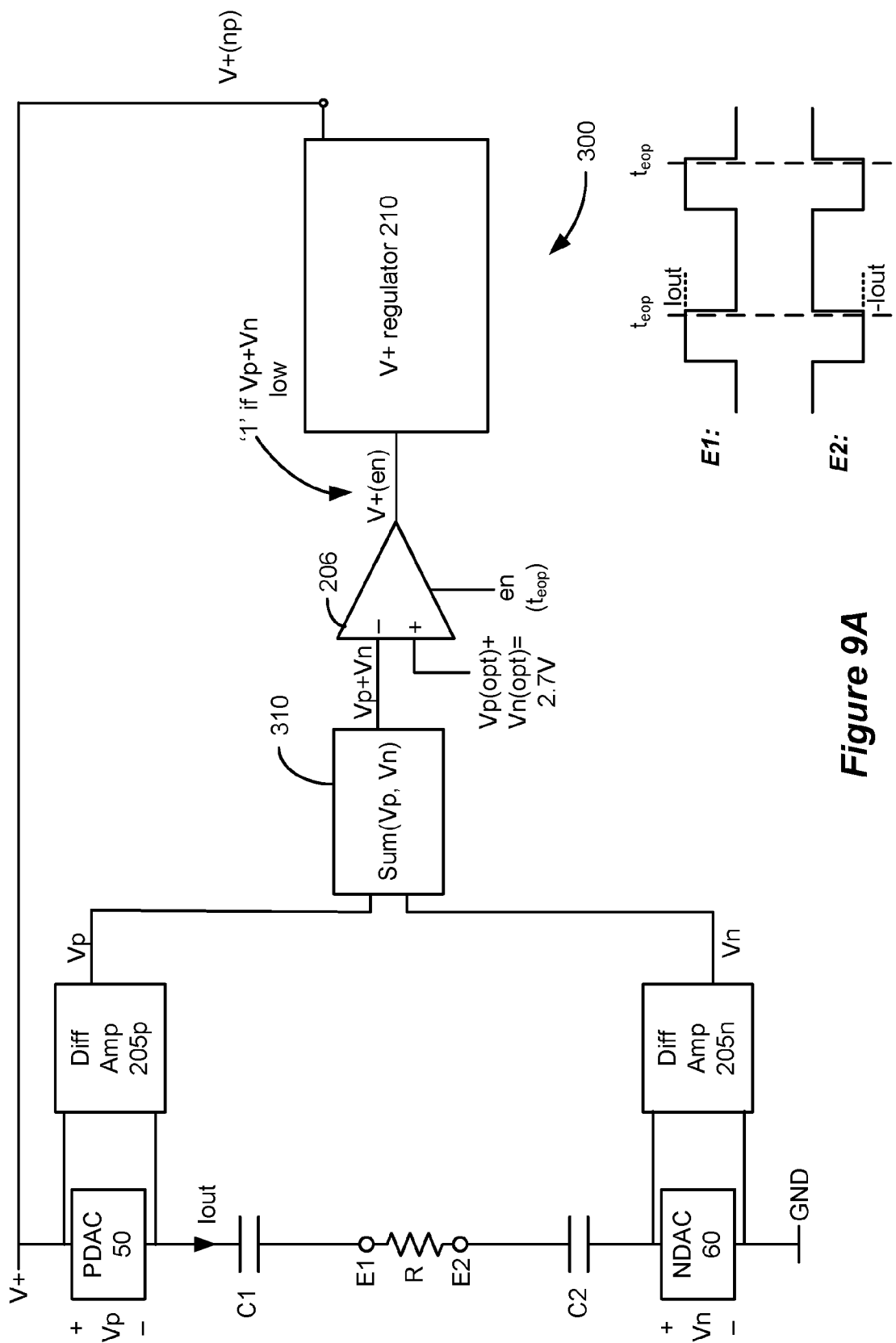
FIGS. 9A and 9B illustrate an improved compliance voltage generation circuit, in accordance with an embodiment of the present invention, using an analog summing circuit.

FIG. 9A shows another example of improved V+ generation circuitry 300 for adjusting V+(np) on a pulse-by pulse basis. In this example, the voltage drops Vp and Vn across active PDAC 50 and NDAC 60 are again measured by diff amps 205. However, in this example, these voltage drops are summed at an analog summing circuit 310. The analog sum Vp+Vn is sent to the inverting inputs of a comparator 206. The non-inverting input is provided with the sum of the optimal values for these voltages drops Vp(opt)+Vn(opt), or 2.7V using the values for these optimal values disclosed earlier. As noted earlier, Vn(opt)=1.2V, Vp(opt)=1.5V, or their sum, can be generated using tunable bandgap reference voltage generators (not shown). The comparator 206 is enabled to compare the summed measured values to the summed optimal values at the end of the pulse ($t_{eop}$) to provide the V+(en) signal to the V+ generator 210, which generator can be constructed and otherwise operates as previously discussed with reference to FIG. 7B.

As so constructed, the goal of V+ generation circuitry 300 is to adjust V+(np) on a pulse-by-pulse basis to ensure that the sum of Vp and Vn is maintained at its optimal summed value. Note that in this example circuit 300, it is not known how Vp or Vn might be individually varying. Thus, for example, the NDAC 60 may be "weak," such that Vn is actually below its optimal value of Vn(opt)=1.2V, while PDAC 50 may be "strong," such that Vp is actually above its optimal value of Vp(opt)=1.5V. Even if one of Vp or Vn is not optimal, optimizing their sum by adjusting V+(np) in real time will still generally allow for proper delivery of the stimulation currents given the serial connection between the PDAC 50 and the NDAC 60.

Figure 9B:
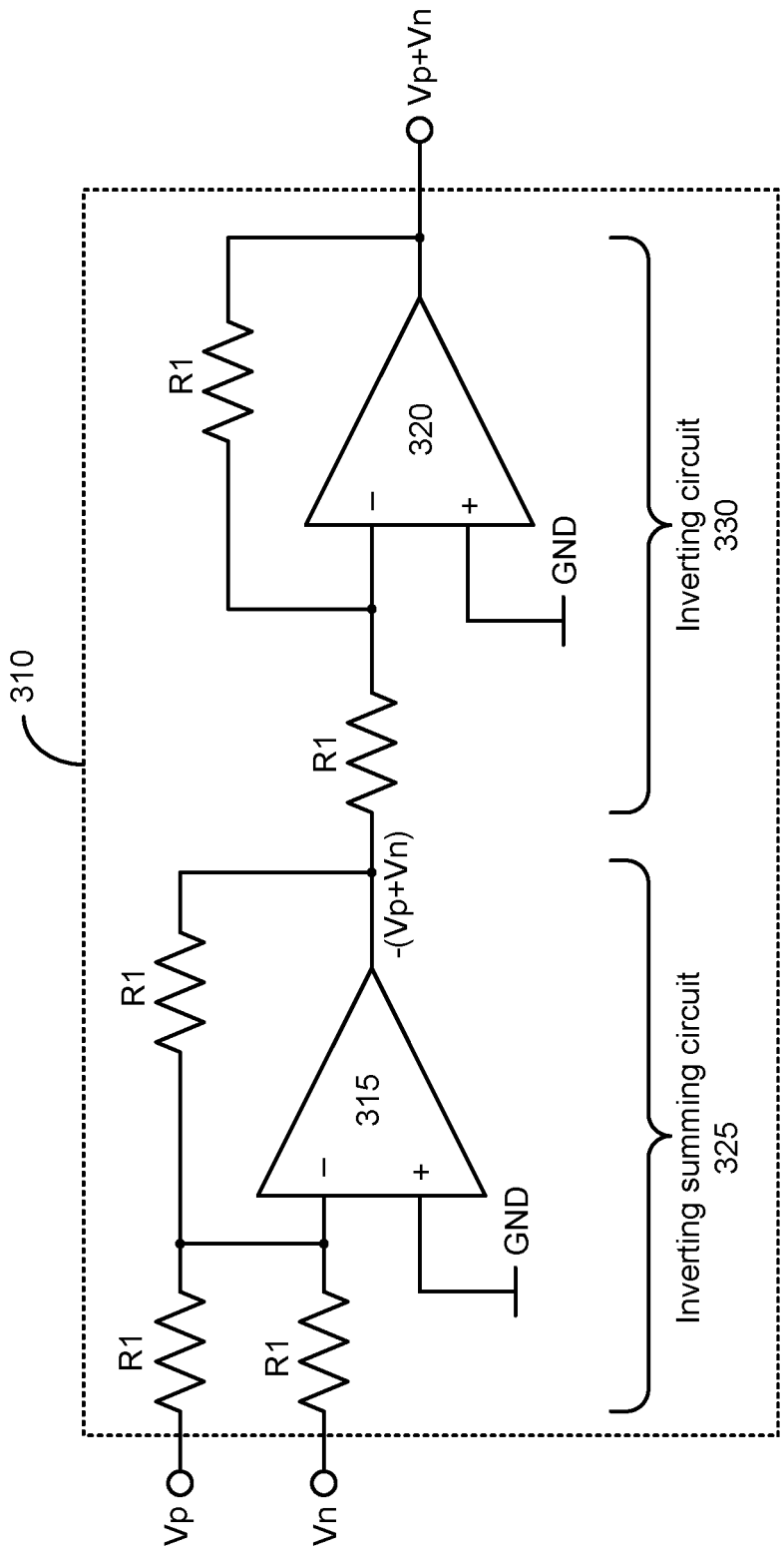

Analog summing circuit 310 is shown in detail in FIG. 9B, and comprises an inverting summing circuit 325, which uses an operational amplifier 315 and a resistive network to produce the inverse of the sum (−(Vp+Vn)). Inverting summing circuits 325 are well known and are not further explained. The inverted sum is then input to an inverting circuit 300. The inverting circuit 330 also comprises an operational amplifier 320 and a resistive network, and operates to invert the input to produce the desired sum Vp+Vn. Again, inverting circuits 330 are well known and are not further explained.

Figure 10A:
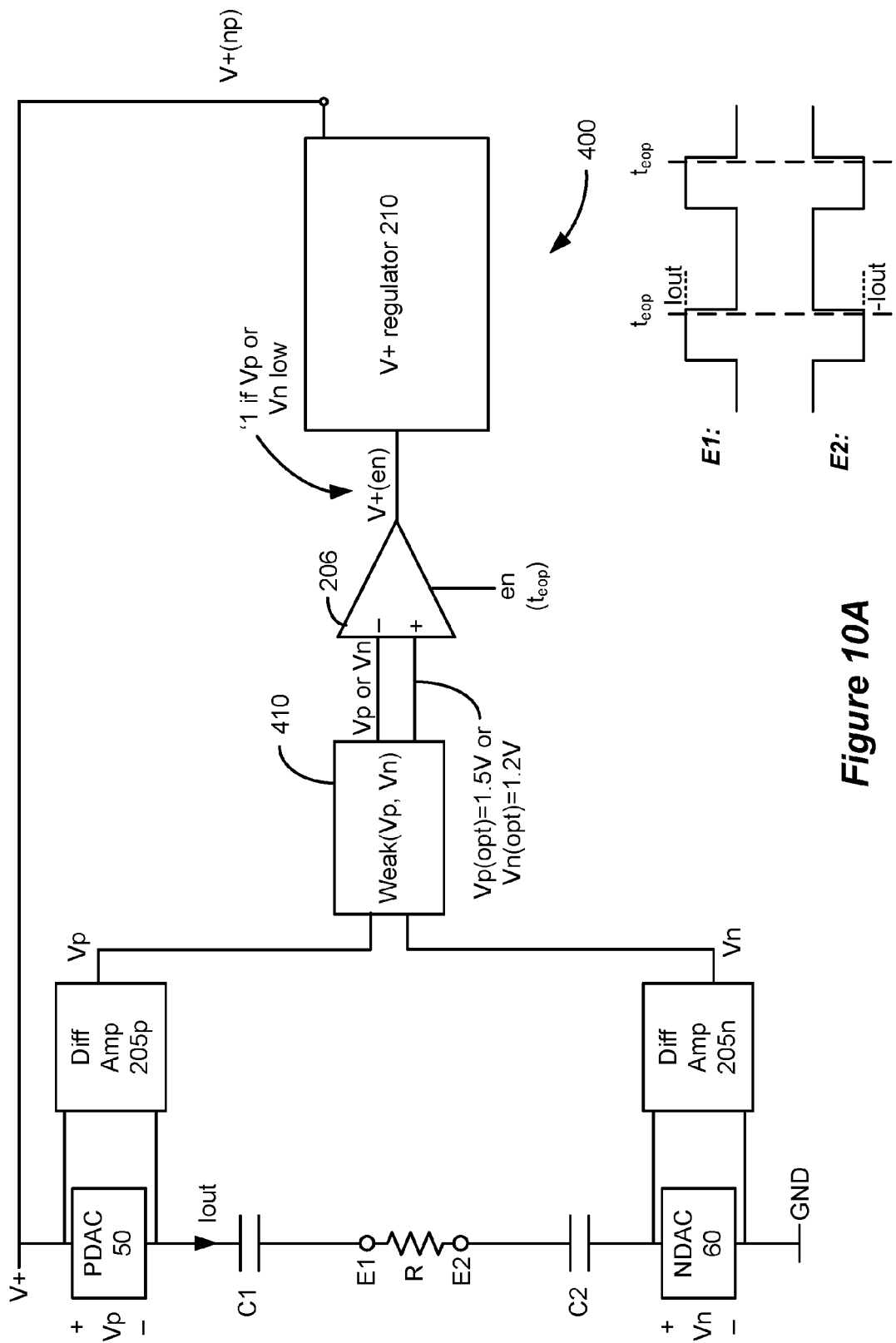
FIGS. 10A-10C illustrate an improved compliance voltage generation circuit, in accordance with an embodiment of the present invention, using weakest value selection circuitry.
Figure 10B:
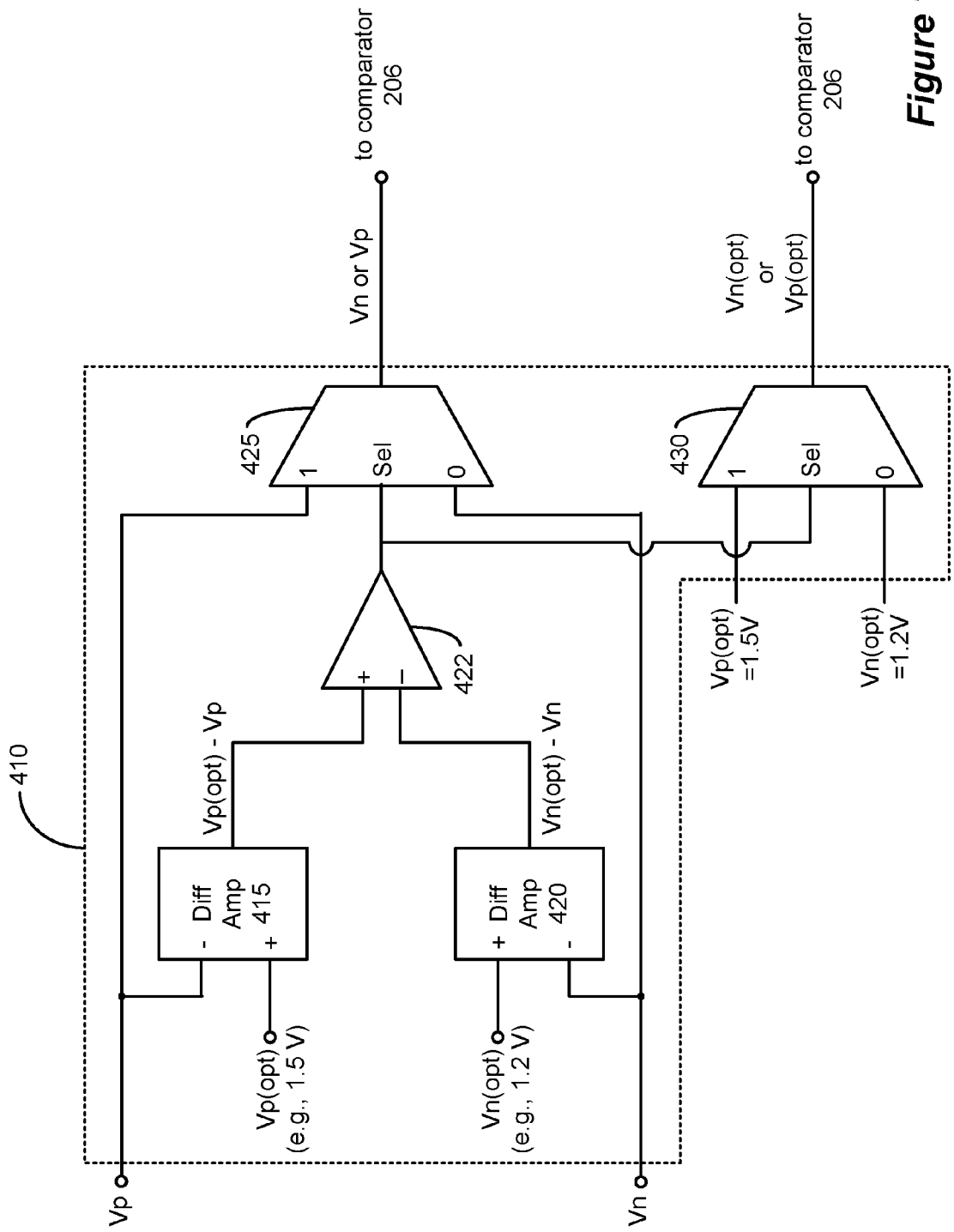

Another modification 400 is shown in FIGS. 10A and 10B. In this example of the improved V+ generation circuitry 400, both of the voltage drops across the PDAC 50 and the NDAC 60, Vp and Vn, are once again monitored. However, in this example, V+(np) is established and controlled by the weaker of Vp and Vn.

FIG. 10A shows the circuitry used, which is largely similar to that shown in FIG. 9A, and thus similar aspects are not again discussed. Different to the embodiment of FIG. 10A is the use of selection circuitry 410. Selection circuitry 410 selects which of Vp or Vn is the weakest, and passes that weakest value and its optimal value to comparator 206 to determine whether that weakest value is below the optimal value. If so, V+(en) is set to '1', which controls the V+ regulator 210 to increase V+(np) as described earlier.

Selection circuitry 410 is shown in further detail in FIG. 10B. Vp and Vn are input to the inverting input of differential amplifiers 415 and 420 respectively. The non-inverting inputs are respectively provided with Vp(opt) and Vn(opt), which again can be generated using tunable bandgap reference voltage generators. The diff amps 415 and 420 output the differences in their inputs, and those outputs are provided to a comparator 422, which controls multiplexers 425 and 430. If Vp(opt)−Vp is greater than Vn(opt)−Vn, which suggests that the PDAC (Vp) is weaker, then the comparator 422 outputs a '1', and Vp and Vp(opt) are passed to the comparator 206 via 425 and 430 respectively. If Vn(opt)−Vn is greater than Vp(opt)−Vp, which suggests that the NDAC (Vn) is weaker, then the comparator 422 outputs a '0', and Vn and Vn(opt) are passed to the comparator 206. Thus, the weaker of Vp or Vn at any given time is used to control the V+ regulator 210, which will in turn raise V+(np) to bring that weaker value back to its optimal level.

Figure 10C:
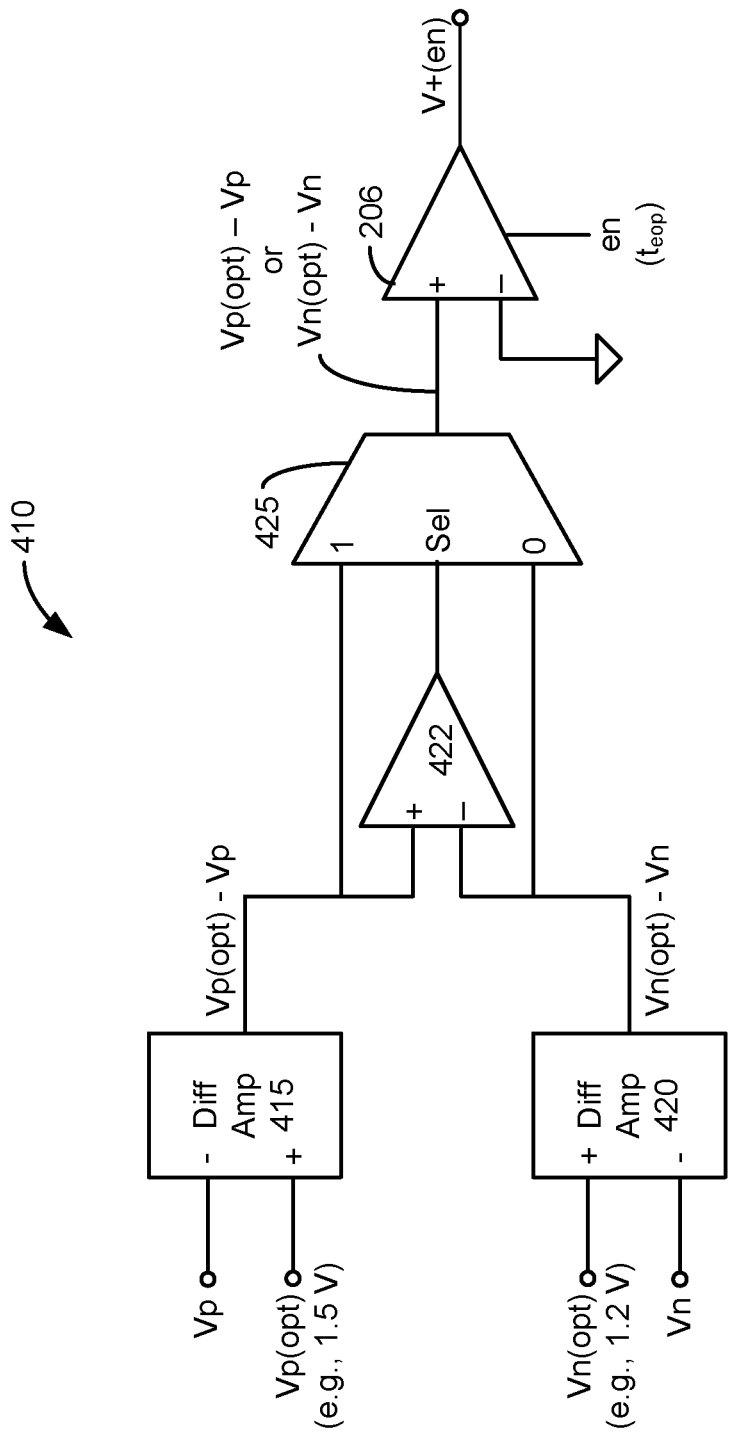

FIG. 10C shows simplified circuitry for using the weaker of Vp or Vn to control the V+ regulator 210. As in FIG. 10B, Vp and Vn are input to the inverting input of differential amplifiers 415 and 420 respectively. The non-inverting inputs are respectively provided with Vp(opt) and Vn(opt). The diff amps 415 and 420 output the differences in their inputs, and those outputs are provided to a comparator 422, which controls a multiplexer 425. If Vp(opt)−Vp is greater than Vn(opt)−Vn, which suggests that the PDAC (Vp) is weaker, then the comparator 422 outputs a '1', and Vp(opt)−Vp is passed to the non-inverting input of comparator 206. The inverting input of comparator 206 in this example is grounded. If Vp(opt)−Vp is positive, suggesting that Vp is too low, comparator 206 outputs V+(en)=1 to the boost converter 220, likely turning it on. If negative, suggesting that Vp is not too low even if it is weaker than Vn, V+(en)=0, likely turning the boost converter 220 off. If Vn(opt)−Vn is greater than Vp(opt)−Vp, which suggests that the NDAC (Vn) is weaker, then the comparator 422 outputs a '0', and Vn(opt)−Vn is passed to the comparator 206, which will likewise assess based on the polarity of this difference whether V+(en) should be set to '1' or '0'. The result is otherwise the same as discussed above with respect to FIG. 10B: the weaker of Vp or Vn at any given time is used to control the V+ regulator 210, which will in turn raise V+(np) to bring that weaker value back to its optimal level.

The disclosed circuitry is extendable to the control of multiple compliance voltages. Consider FIG. 11A, which has two compliance voltages, V1+ and V2+. As shown, these compliance voltages are used to power two different current paths, which may issue pulses at the same or different times. V1+ is used to provide a stimulation current Iout1 from E1 to E2 under the control of PDAC 50a and NDAC 60c; while V2+ is used to provide a stimulation current Iout2 from E3 to E4 under the control of PDAC 50b and NDAC 60d. Any of the electrodes, PDACs, or NDACs could have been chosen for this example, depending on the current distribution architecture used.

Figure 11A:
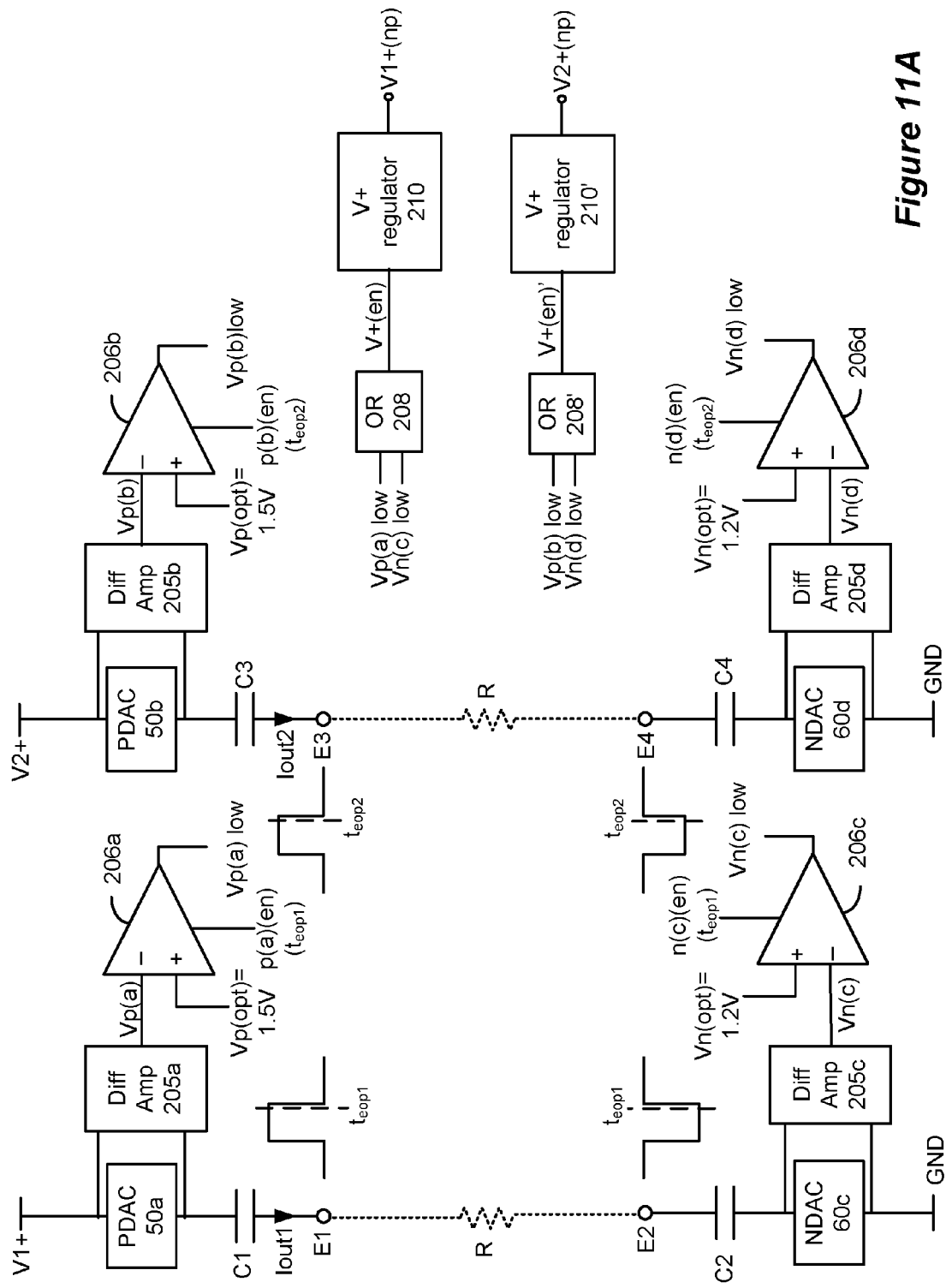
FIGS. 11A-11C illustrate multiple compliance voltage generators being used for generating multiple compliance voltages, in accordance with an embodiment of the present invention.

These current paths can be independently controlled, and accordingly, the V+ generation circuitry can be duplicated, as shown in FIG. 11A. Thus, Vp(a) and Vn(c) from the Iout1 current path are compared to optimal values and used to create signals Vp(a) low and Vn(c) low that are input to OR gate 208, which produces control signal V+(en) for V+ regulator 210, which produces V1+(np) for the Iout1 current path. Likewise, Vp(b) and Vn(d) from the Iout2 current path are compared to optimal values and used to create signals Vp(b) low and Vn(d) low that are input to OR gate 208', which produces control signal V+(en)' for V+ regulator 210', which produces V2+(np) for the Iout2 current path. Thus, optimal values for both compliance voltages V1+ and V2+ are set, in this case using the OR gate technique discussed earlier with reference to FIGS. 6A-8.

Figure 11B:
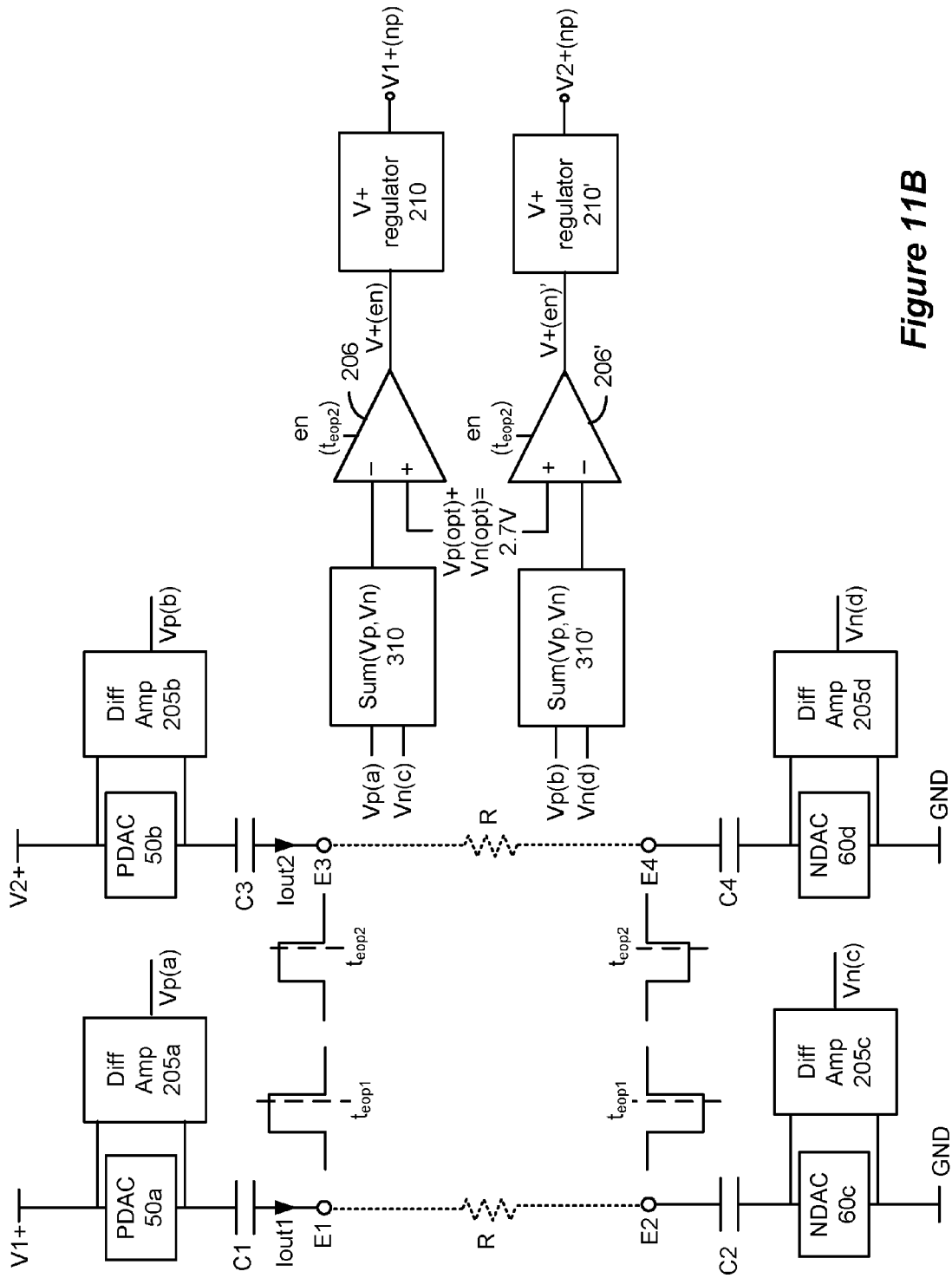
Figure 11C:
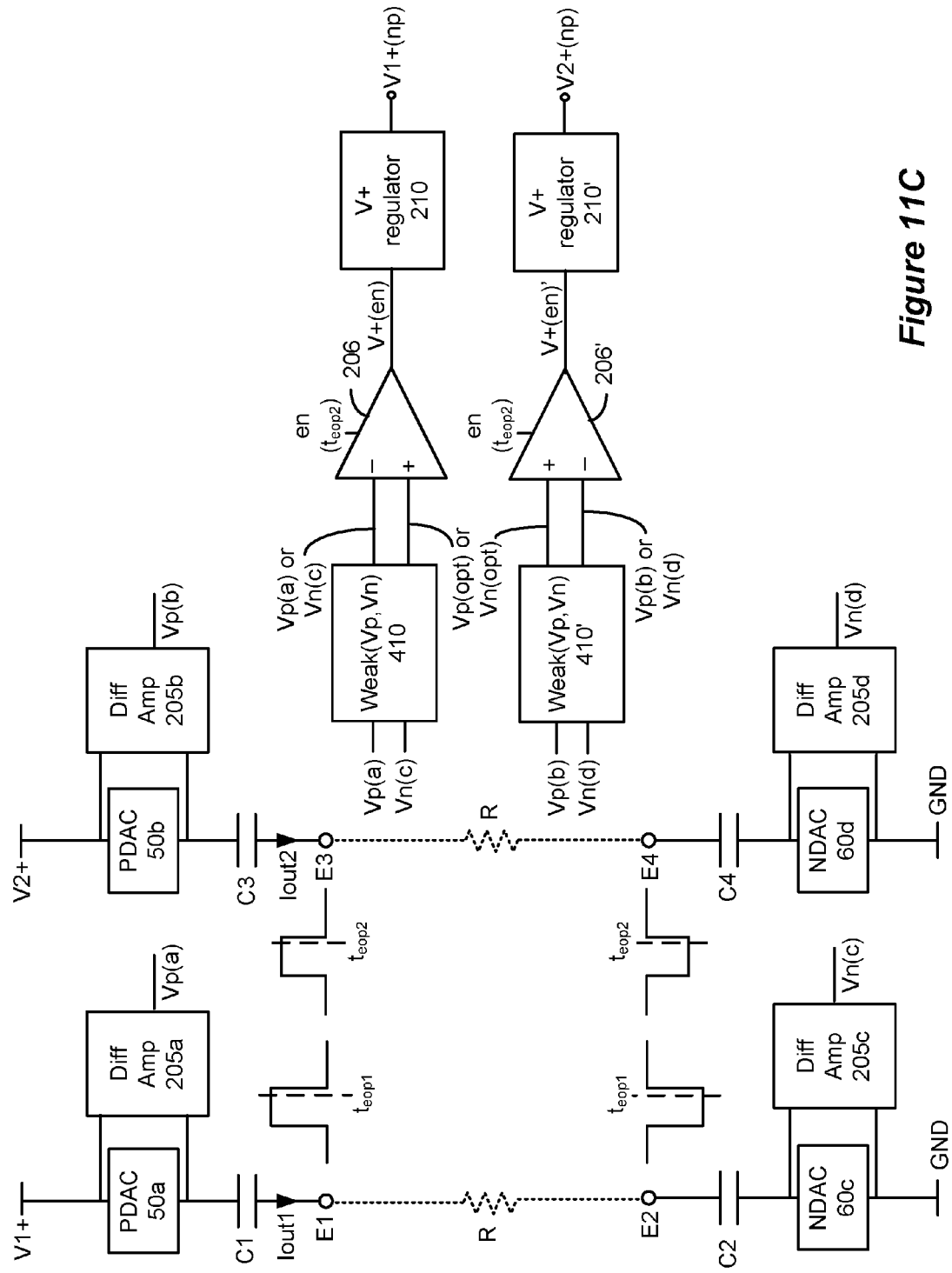

FIG. 11B shows a similar example to that illustrated in FIG. 11A, but modified to optimize the sum of the voltage drops in each of the current paths, as was discussed previously with respect to FIGS. 9A and 9B. FIG. 11C is also similar, but modified to optimize the compliance voltages using the weaker of the voltage drops in each of the current paths, as was discussed previously with respect to FIGS. 10A and 10B.

Figure 12:
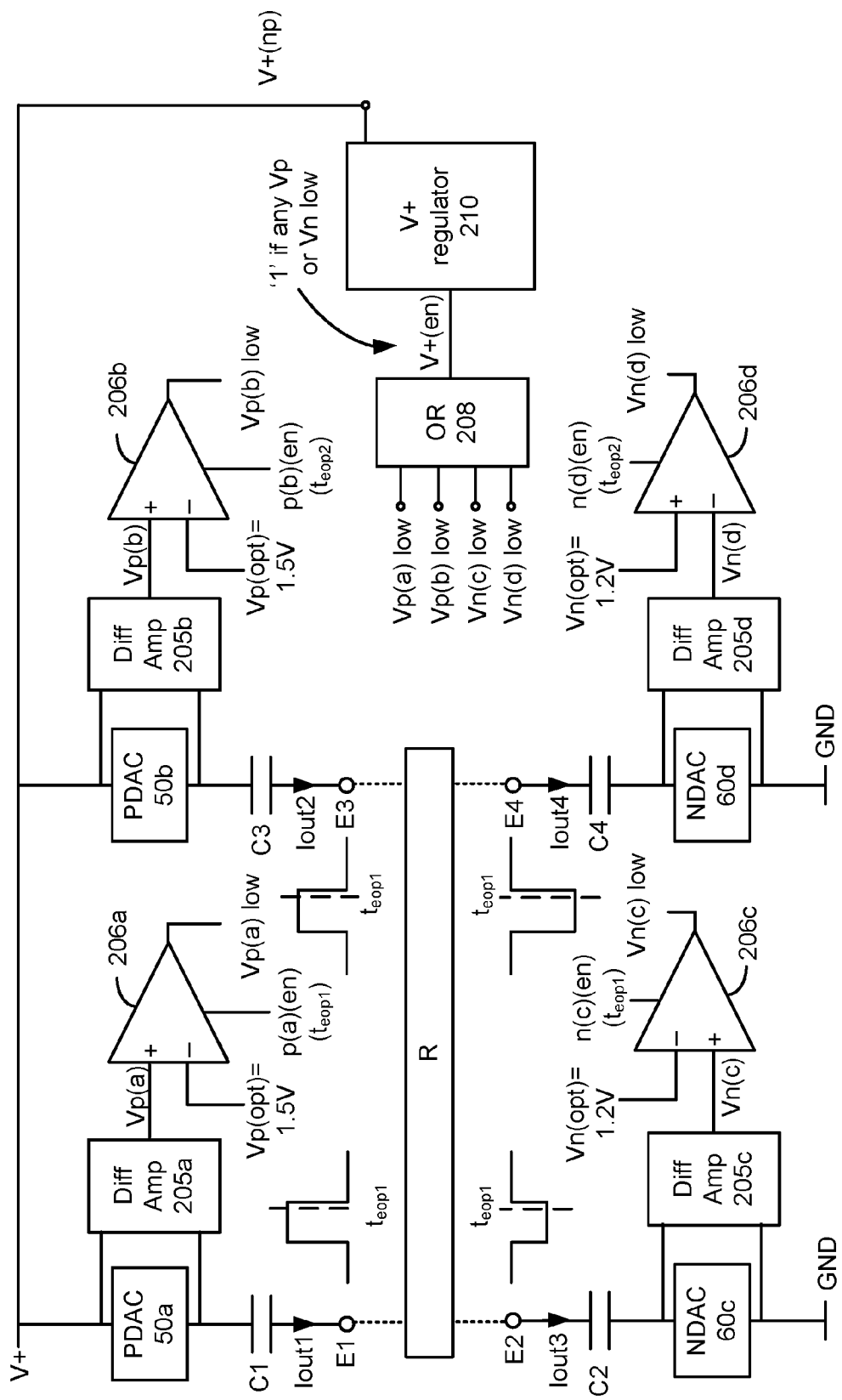
FIG. 12 illustrates the compliance voltage generation circuit being used to generate a compliance voltage when more than two current sources and/or more than two current sinks are active, in accordance with an embodiment of the present invention.

The disclosed circuitry is extendable to the control the compliance voltage even when more than one PDAC and/or more than one NDAC is active at a given time. Consider FIG. 12, which uses two PDACs (50a, 50b) to source two different currents (Iout1, Iout2) to electrodes E1 and E3, and which uses two NDACs (60c, 60d) to sink two different currents (Iout3, Iout4) from electrodes E2 and E4. Again, any of the electrodes, PDACs, or NDACs could have been chosen for this example. (Note also that Iout1+Iout2=Iout3+Iout4 to ensure that the sum of all currents at the tissue equals zero). The voltage drops across the active PDACs and NDACs (Vp(a), Vp(b), Vn(c), Vn(d)) are compared against optimal values and the results of those comparisons are input to OR gate 208, which as before will determine whether any voltage drop is low, and will control the V+ regulator 210 accordingly to adjust V+(np) for the next pulse. Although not shown, further processing to sum certain of the voltage drops, to choose certain weaker of the voltage drops, etc., could also be used, similar to what was described earlier.

Figure 13:
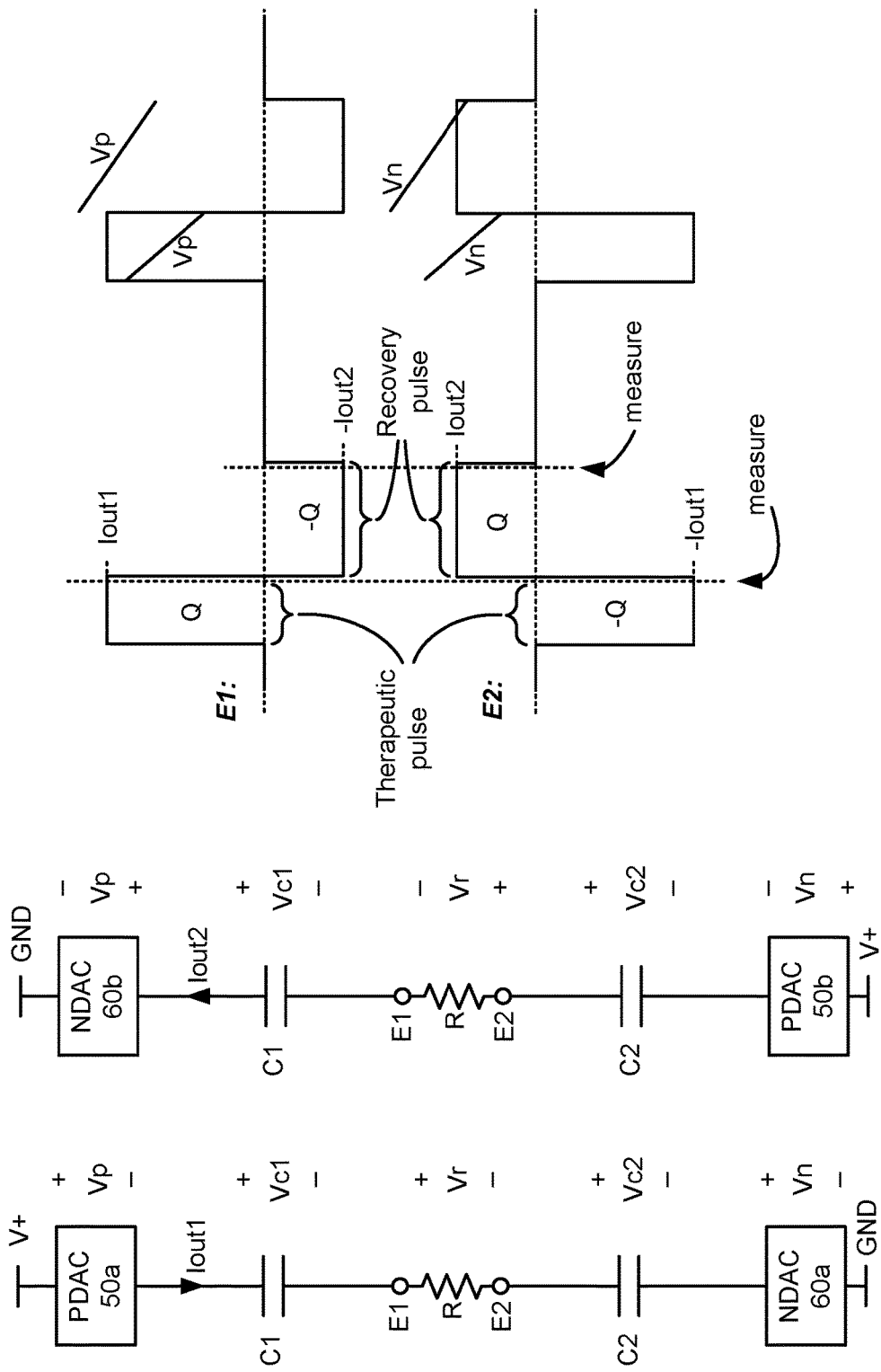
FIG. 13 illustrates use of the improved compliance voltage generation circuits with biphasic pulses.

FIG. 13 illustrates a biphasic pulse, and discusses how the various examples of the disclosed V+ generation circuitry may be used with such a pulse. As is known, a biphasic pulse has two phases: a therapeutic pulse phase of magnitude Iout1, followed by a recovery pulse phase, which in this example has a lower magnitude Iout2 and is of opposite polarity. The recovery pulse is generally not mandated by patient therapy, but is instead used to remove charge that accumulated on the decoupling capacitors during the larger-magnitude therapeutic pulse. As noted earlier, the decoupling capacitors will store charge as current passes through them during a therapeutic pulse, which is generally undesired. Reversing the current through those capacitances during the recovery pulse seeks to actively recover such stored charge. To actively recover stored change in this fashion, it is preferable that the same amount of charge (Q) be passed in the recovery pulse as was passed in the therapeutic pulse. This can be done by making the amplitude and pulse width of the recovery pulse equal to that of the therapeutic pulse, or, as shown, by making the recovery pulse of longer duration and lower amplitude so that it has less effect on the patient.

Just like the therapeutic pulses, the recovery pulses are generated by a PDAC and NDAC. (If a dedicated architecture is used as in FIG. 2A, the other of the dedicated PDAC or NDAC for the active electrodes would be used during the recovery phase; if a distributed architecture is used as in FIG. 2B, the same PDACs and NDACs can be used, with the switching matrices 70P and 70N now coupling them to the other electrode during the recovery phase).

Because the recovery phase is an active pulse generated by the DACs, concerns may arise whether the compliance voltage is sufficient, or efficient, in generating such pulses. As such, it is also useful to measure the voltage drops across the active DACs during the recovery pulses as well, as shown in FIG. 13. As with the therapeutic pulses, it is often sensible to measure the recovery pulses at or near their end. This is because Vp and Vn will also be at their worst (lowest) case at the end of such pulses. The reason again relates to the decoupling capacitors which were charged during the therapeutic pulse. When the direction of the current is reversed during the recovery pulse, the voltages stored across the decoupling capacitors (Vc1, Vc2) are now of opposite polarity with respect to V+, and as a result Vn and Vp are relatively high to counteract these now negative voltages. As these stored voltages are gradually reduced during the recovery pulse, Vp and Vn no longer have to offset such a large negative voltage and will start to fall.

It can be difficult to know whether the measurements taken at the end of the therapeutic pulse or the measurements taken at the end of the recovery pulse will provide a worst case that should be assessed for setting V+(np). If the two pulses are of the same magnitude, Vp and Vn would be expected to be roughly the same. If the two pulses are of different magnitudes, as shown in FIG. 13, Vp and Vn would be higher during the recovery pulse, because the voltage drop across the tissue (Vr) would be less. In any event, measuring both will ensure that V+(np) is kept to an optimal level. For example, if the voltage drops Vp and Vn are lowest during the therapeutic pulse, then those measurements will be used to set V+(np). The measurements taken during the recovery pulses, when Vp and Vn are relatively high, may result in deactivating the boost converter 220, but if necessary the boost converter 220 will once again be enabled when the subsequent therapeutic pulse is measured. Thus, similar to what was illustrated in FIG. 7C, allowing the V+ generation circuitry to operate will still result in V+(np) stabilizing around an optimal value V+(opt) for the therapeutic pulses (even if V+(np) is in fact inefficiently high during the recovery pulses).

Figure 14A:
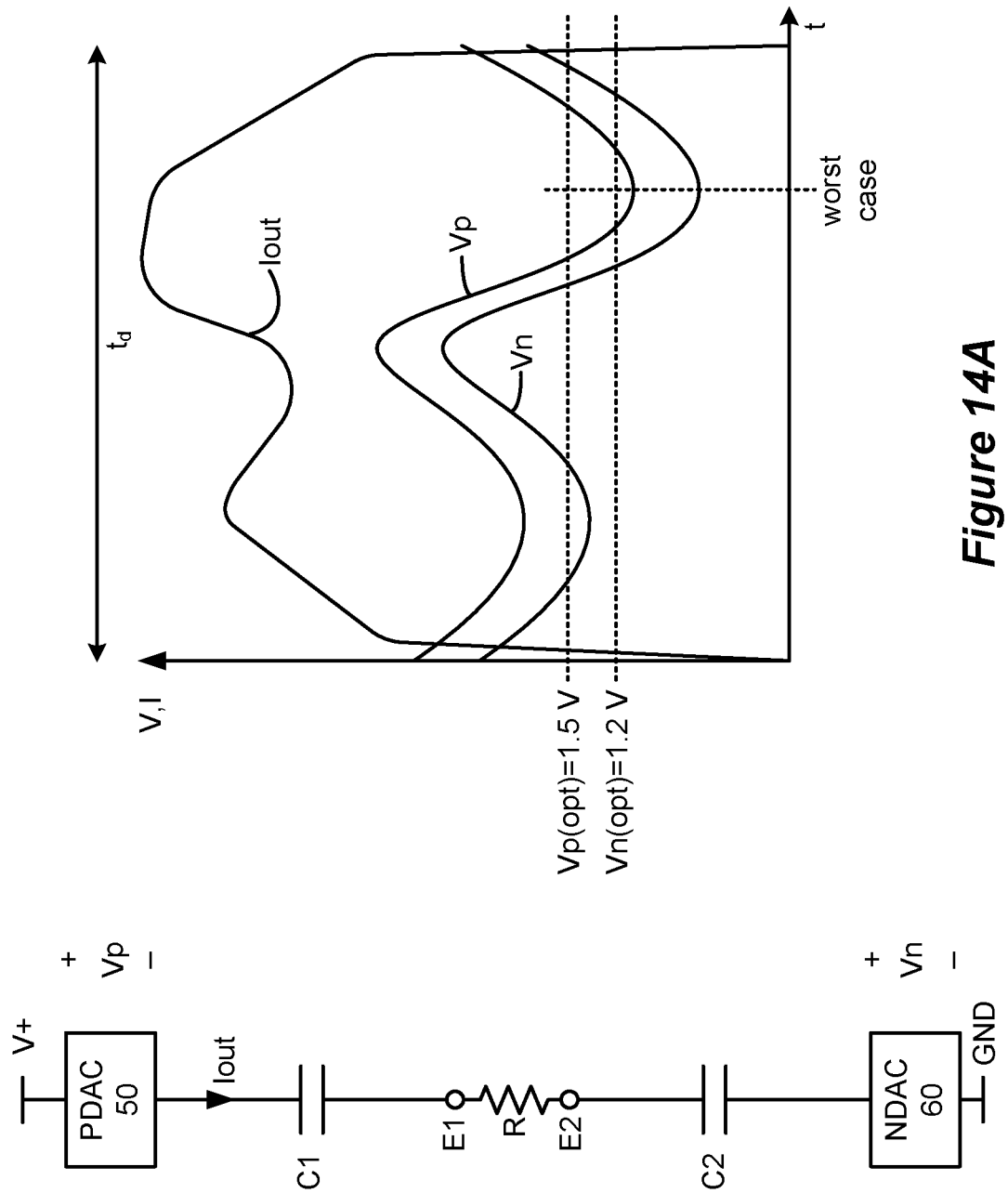
FIGS. 14A-14C illustrate minimum determining circuitry useable in the improved compliance generation circuitry.

Although it has been assumed to this point that it is generally better to measure the voltage drops at the end of the pulse for the reasons discussed earlier with reference to FIG. 6B, this is not always true. Instead, the optimal measuring point can depend on the shape of the pulse the DACs are providing. Consider the non-constant current pulse of FIG. 14A. Different factors affect when the voltage drops across the DACs are at their lowest—i.e., the worst case in which the DACs are at greatest risk of entering sub-saturation. Higher currents will yield higher voltage drops Vr, in the patient's tissue, R, which will generally reduce Vp and Vn. And as discussed earlier, current will charge the decoupling capacitors over time, which also will generally reduce Vp and Vn, and higher currents will charge them more quickly. It can therefore be difficult to know for any given pulse when the worst case (lowest Vp, Vn) will occur during the pulse, and thus when it would be best to measure the pulse to set the compliance voltage. In other words, it can be difficult for the control circuitry 85 to provide enable signals to the comparators at appropriate times to determine whether the voltage drops are high or low.

Figure 14B:
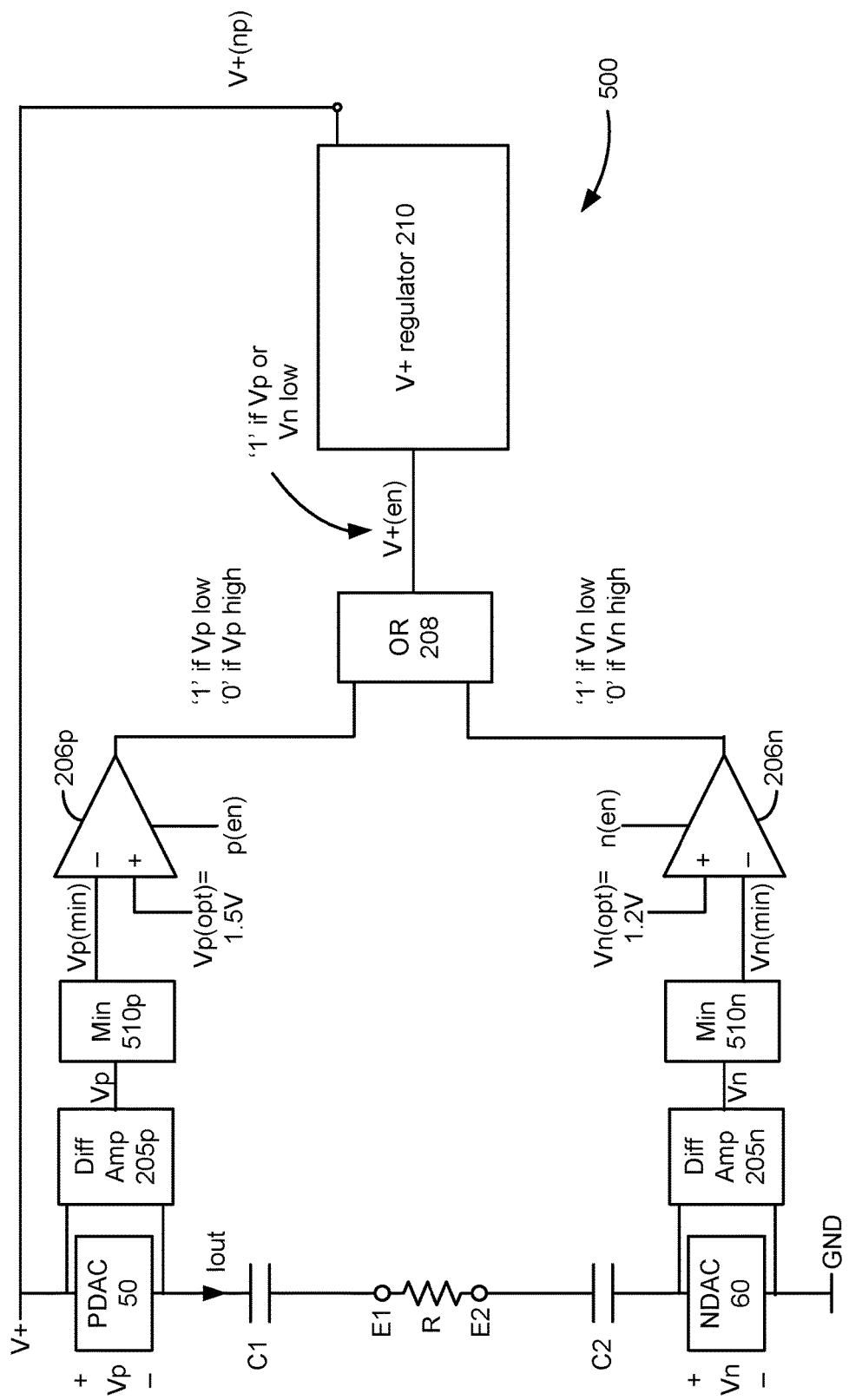
Figure 14C:
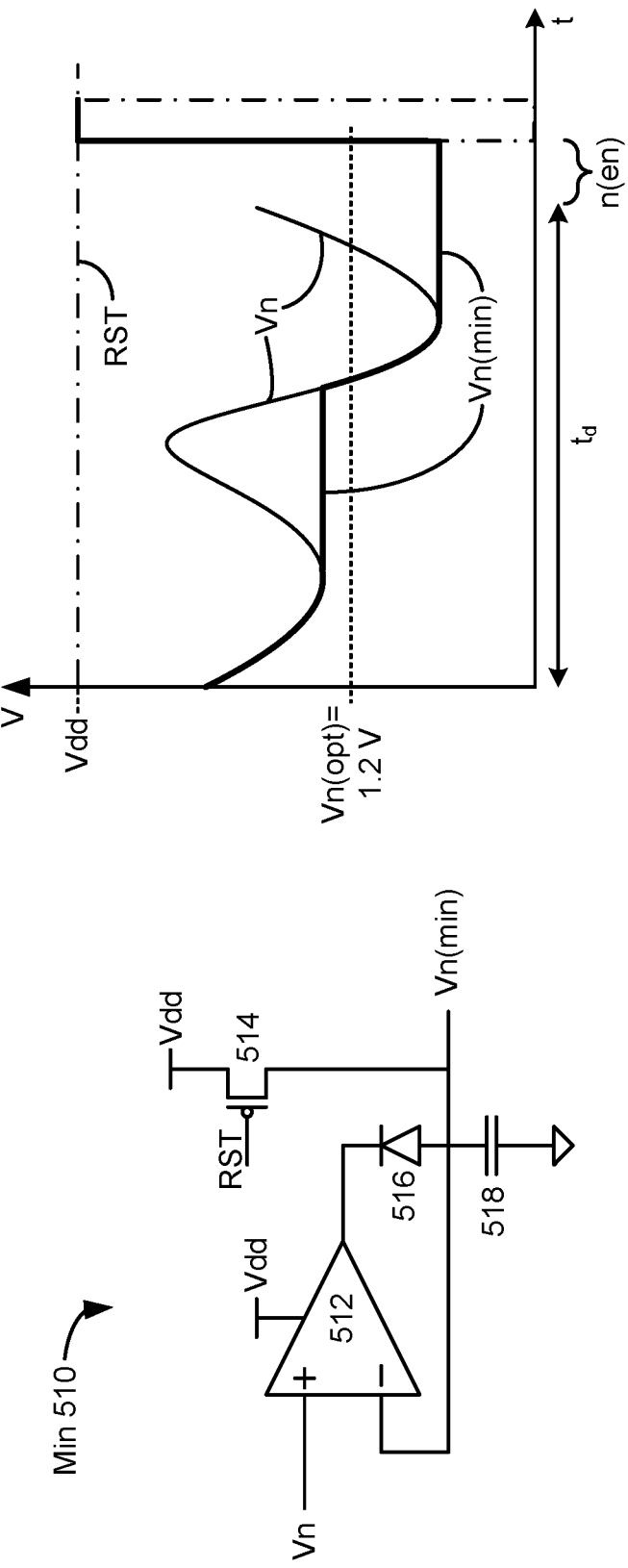

In recognition of this fact, FIGS. 14B and 14C disclose another example of improved V+ generation circuitry 500 that automatically determines and measures the worst case wherever it appears in the pulse, even if that worst case varies in time from pulse to pulse. A simple case of measurement of a single PDAC and NDAC are shown, which measurements are received by an OR gate 208. However, any of the modifications previously discussed could also be illustrated. In FIG. 14B, the measured voltage drops Vp and Vn are provided to minimum determining circuits 510. As will be discussed in greater detail with reference to FIG. 14C, minimum determining circuits 510 samples the voltage drops during the duration of the pulse, and store the minimum values, Vp(min) and Vn(min). These minimum values are sent to comparators 206 for comparison to optimal values Vp(opt) and Vn(opt) after the pulse, which can then be used to adjust V+(np) for the next pulse in any of the ways previously discussed.

The minimum determining circuit 510 is shown in FIG. 14C, and its operation is illustrated with respect to determining a minimum value for Vn (Vn(min). Although not illustrated, similar circuitry would be used to determine Vp(min) from Vp. The circuit 510 comprises an operational amplifier (op amp) 512, and the analog voltage drop (Vn) is provided to its non-inverting input. A diode 516 is coupled between the output of the op amp 512 and its inverting input, and a storage capacitor 518 is provided between the inverting input and ground. Because of the feedback provided by the diode, the output (Vn(min)) will track the input (Vn) so long as the diode 516 is conducting, which can only occur when the input is decreasing. If the input is increasing, the comparator outputs a '1' (i.e., Vdd), which reverse biases the diode 516 and decouples the input from the output. The result is that the minimum of the input is stored across the storage capacitor 518 at any point in time, and so at the end of the pulse, the minimum value for Vn is stored.

After the pulse has ended, the minimum voltage remains stored on the capacitor 518, and can then be compared and used to establish V+(np) in the ways previously mentioned. Specifically, the control circuitry 85 can issue an enable signal (n(en)) to the comparator 206 after the pulse has ended. Again, the timing of the pulses is known to the control circuitry 85, and so the enable signal can be timed accordingly. Afterwards, a reset switch 514 in the minimum determining circuit 510 can precharge the sampling capacitor 518 to a high voltage (Vdd) in preparation for the voltage drop measurement of the next pulse.

It is preferable to initialize the V+ generation circuitry as discussed with reference to FIG. 7C (by initializing the count and V+(np) to maximum values) when therapy settings are changed, and thereafter to simply allow the V+ generation circuitry to run to keep V+(np) at optimal levels pulse by pulse. However, this is not strictly necessary. Instead, the V+ generation need not be initialized to any particular values, even if this might result in some number of pulses not providing optimal therapy. Alternatively, the V+ generation circuitry can cease running after a baseline for V+(np) has been established, and perhaps can be re-run from time to time to reset V+(np) in case conditions have changed.

While Vn(opt) and Vp(opt) have been disclosed as comprising different values, it should be understood that these optimal values across the current source and current could also be the same for a given architecture. In other words, in the claims, the first and second optimal voltages can comprise the same value or can be different.

Depending on the implementation, it may not always be required to use two different current generators, such as a source (PDAC) and a sink (NDAC). Instead, only one current generator can be used on either the sourcing or sinking side of the current, with the other side sourcing or sinking current from a passive reference voltage. Moreover, the current generators can comprise any sorts of generators used to produce currents, and current sources and sinks as used herein should therefore be construed to cover voltage sources as well.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. Circuitry configured to adjust a compliance voltage in an implantable stimulator device, comprising:
   a current generator configured to provide a current pulse to at least one electrode;
   minimum determining circuitry configured to monitor a voltage across the current generator at different points in time during the current pulse and to determine a minimum value of the monitored voltages; and
   regulator circuitry configured to adjust the compliance voltage that powers the current generator, wherein the regulator circuitry is controlled by a control signal derived from the minimum value.

2. The circuitry of claim 1, wherein the minimum determining circuita comprises:
   an amplifier configured to receive the monitored voltages at a first input, and the minimum value at a second input;
   a diode coupled between an output of the amplifier and the minimum value; and
   a storage capacitor coupled between the minimum value and ground.

3. The circuitry of claim 2, wherein the minimum determining circuitry further comprises a pull up transistor configured to pull up the minimum value after the minimum value of the voltage across the current generator has been determined.

4. The circuitry of claim 1, wherein the current generator comprises a current source configured to source the current pulse to the at least one electrode.

5. The circuitry of claim 1, wherein the current generator comprises a current sink configured to sink the current pulse from the at least one electrode.

6. The circuitry of claim 1, wherein the compliance voltage is configured to provide power to the current generator.

7. Circuitry configured to adjust a compliance voltage in an implantable stimulator device, comprising:
   a source circuit coupled to a compliance voltage, wherein the source circuit is configured to provide a first current pulse to at least a first electrode;
   a sink circuit coupled to a reference voltage, wherein the sink circuit is configured to sink the first current pulse from at least a second electrode;
   first minimum determining circuitry configured to monitor a first voltage across the source circuit at different points in time during the first current pulse and to determine a minimum first value of the monitored first voltages;
   second minimum determining circuitry configured to monitor a second voltage across the sink circuit at different points in time during the first current pulse and to determine a minimum second value of the monitored second voltages; and
   regulator circuitry configured to adjust the compliance voltage, wherein the regulator circuitry is controlled by a control signal derived from the minimum first value and the minimum second value.

8. The circuitry of claim 7, further comprising:
   a first comparator configured to compare the minimum first value to an optimal first voltage and to produce a first digital signal indicating whether the minimum first value is high or low relative to the optimal first voltage; and
   a second comparator configured to compare the minimum second value to an optimal second voltage and to produce a second digital signal indicating whether the minimum second value is high or low relative to the optimal second voltage,
   wherein the control signal is derived from the first and second digital signals.

9. The circuitry of claim 8, wherein the control signal enables the regulator circuitry when either the first or second digital signal indicates that the minimum first or second value is low compared respectively to the first or second optimal voltage.

10. The circuitry of claim 8, wherein the first and second comparators compare the minimum first and second values respectively to the optimal first and second voltages after the first current pulse.

11. The circuitry of claim 7, further comprising a summing circuit to add the first minimum value and the second minimum value to produce a summed signal, wherein the control signal is derived from the summed signal.

12. The circuitry of claim 11, further comprising a comparator configured to compare the summed signal to an optimal summed signal and to produce the control signal indicating whether the summed signal is high or low relative to the optimal summed signal.

13. The circuitry of claim 7, wherein the control signal is digital.

14. The circuitry of claim 7, wherein the regulator circuitry is configured to adjust the compliance voltage for a next current pulse in accordance with the control signal.

15. The circuitry of claim 7, further comprising a first amplifier configured to monitor the first voltage across the source circuit, and a second amplifier configured to monitor the second voltage across the sink circuit.

16. A method for operating an implantable stimulator device, the implantable stimulator device having a current generator to provide a current pulse to at least one electrode, the method comprising: monitoring a voltage across the current generator at different points in time during the current pulse; determining a minimum value of the monitored voltages; deriving a control signal from the minimum value; and controlling, using the control signal, a regulator circuitry to adjust a compliance voltage that powers the current generator.

17. The method of claim 16, wherein the voltages are monitored and the minimum value is determined using
   an amplifier configured to receive the monitored voltages at a first input, and the minimum value at a second input;
   a diode coupled between an output of the amplifier and the minimum value; and
   a storage capacitor coupled between the minimum value and ground.

18. The method of claim 16, wherein the current generator comprises a current source configured to source the current pulse to the at least one electrode.

19. The method of claim 16, wherein the current generator comprises a current sink configured to sink the current pulse from the at least one electrode.

20. The method of claim 16, wherein the compliance voltage is used to power the current generator.

* * * * *